US007678561B2

(12) United States Patent
Mayfield

(10) Patent No.: US 7,678,561 B2
(45) Date of Patent: Mar. 16, 2010

(54) ROBUST EXPRESSION OF A BIOACTIVE MAMMALIAN PROTEIN IN CHLAMYDOMONAS CHLOROPLAST

(75) Inventor: Stephen P. Mayfield, Cardiff, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 11/801,506

(22) Filed: May 9, 2007

(65) Prior Publication Data

US 2007/0298050 A1 Dec. 27, 2007

Related U.S. Application Data

(60) Provisional application No. 60/799,120, filed on May 9, 2006, provisional application No. 60/903,692, filed on Feb. 26, 2007.

(51) Int. Cl.
*C12N 15/82* (2006.01)
(52) U.S. Cl. .............. 435/257.2; 800/278; 800/288; 435/257.6; 435/468; 435/71.1
(58) Field of Classification Search ............ None
See application file for complete search history.

(56) References Cited

U.S. PATENT DOCUMENTS

| 5,451,513 | A | 9/1995 | Maliga et al. | ............ 800/278 |
| 5,545,817 | A | 8/1996 | McBride et al. | ............ 800/278 |
| 5,545,818 | A | 8/1996 | McBride et al. | ............ 800/279 |
| 2003/0022359 | A1* | 1/2003 | Sayre et al. | ............ 435/257.2 |
| 2003/0170840 | A1* | 9/2003 | McDonald et al. | ............ 435/183 |
| 2003/0211089 | A1 | 11/2003 | Sayre et al. | ............ 424/93.21 |
| 2004/0014174 | A1* | 1/2004 | Mayfield et al. | ............ 435/69.1 |

FOREIGN PATENT DOCUMENTS

WO          WO95/16783          6/1995

OTHER PUBLICATIONS

Manuell et al (2007, Plant Biotechnol. J 5:402-412).*
Minagawa et al (1994, Photosyn. Res. 42:121-131).*
Barnes et al (2005, Mol. Gen. Genet. 274:625-636).*
Manuell et al., "Robust expression of a bioactive mammalian protein in Chlamydomonas chloroplast", *Plant Biotechnology Journal*, 5:402-412 (2007).
Minagawa & Crofts, "A robust protocol for site-directed mutagenesis of the D1 protein in Chlamydomonas reinhardtii: A PCR-spliced psbA gene in a plasmid conferring spectinomycin resistance was introduced into a psbA deletion strain", *Photosynthesis Research*, 42:121-131 (1994).
Franklin et al., "Development of a GFP reporter gene for Chlamydomonas reinhardtii chloroplast," *The Plant Journal* (2002) 30:733-744.
Dong et al., "Co-variation of tRNA abundance and codon usage in Escherichia coli at different growth rates," *Journal of Molecular Biology* (1996) 260:649-663.

Duret, "tRNA gene number and codon usage in the *C. elegans* genome are co-adapted for optimal translation of highly expressed genes," *Trends in Genetics* (2000) 16:287-289.
Goldman et al., "Consecutive low-usage leucine codons block translation only when near the 5' end of a message in *Escherichia coli,*" *Journal of Molecular Biology* (1995) 245:467-473.
Komar et al., "Enhanced expression of the yeast Ure2 protein in *Escherichia coli*: the effect of synonymous codon substitutions at a selected place in the gene," *Biological Chemistry* (1998) 379:1295-1300.
Novy et al., "Overcoming the codon bias of *E.coli* for enhanced protein expression", *inNovations* (2001) 12:1-3.
Morton B. R., "Chloroplast DNA codon use: evidence for selection at the psb A locus based on tRNA availability," *Journal of Molecular Evolution* (1993) 37(3):273-80.
Bock, "Transgenic plastids in basic research and plant biotechnology," *Journal of Molecular Biology* (2001) 312:425-438.
Maul et al., "The *Chlamydomonas reinhardtii* plastid chromosome: islands of genes in a sea of repeats," *The Plant Cell* (2002) 14(11):2659-79.
Gray, "Evolution of organellar genomes," *Current Opinion in Genetics and Development* (1999) 9:678-687.
Barkan and Goldschmidt-Clermont, "Participation of nuclear genes in chloroplast gene expression," *Biochimie* (2000) 82:559-572.
McBride et al., "Controlled expression of plastid transgenes in plants based on a nuclear DNA-encoded and plastid-targeted T7 RNA polymerase," *Proceedings of the National Academy of Sciences in the United States of America* (1994) 91:7301-7305, USA.
Staub and Maliga, uidA, "Accumulation of D1 polypeptide in tobacco plastids is regulated via the untranslated region of the psbA mRNA," *The EMBO Journal* (1993) 12:601-606.
Carrer et al., "Kanamycin resistance as a selectable marker for plastid transformation in tobacco," *Molecular and General Genetics* (1993) 241:49-56.
Svab and Maliga, "High-frequency plastid transformation in tobacco by selection for a chimeric aadA gene," *Proceedings of the National Academy of Sciences in the United States of America* (1993) 90:913-917, USA.
Sidorov et al., "Stable chloroplast transformation in potato: use of green fluorescent protein as a plastid marker," *The Plant Journal* (1999) 19:209-216.

(Continued)

*Primary Examiner*—Anne R Kubelik
(74) *Attorney, Agent, or Firm*—DLA Piper LLP (US)

(57) ABSTRACT

Methods and compositions are disclosed to engineer chloroplast comprising heterologous mammalian genes via a direct replacement of chloroplast Photosystem II (PSII) reaction center protein coding regions to achieve expression of recombinant protein above 5% of total protein. When algae is used, algal expressed protein is produced predominantly as a soluble protein where the functional activity of the peptide is intact. As the host algae is edible, production of biologics in this organism for oral delivery or proteins/peptides, especially gut active proteins, without purification is disclosed.

51 Claims, 7 Drawing Sheets

OTHER PUBLICATIONS

Heifetz, "Genetic engineering of the chloroplast," *Biochimie* (2000) 82(6-7):655-666.

Barnes et al., "Contribution of 5'- and 3'-untranslated regions of plastid mRNAs to the expression of *Chlamydomonas reinhardtii* chloroplast genes," *Molecular Genetics and Genomics* (2005) 274(6): 625-636.

Mayfield and Schultz, "Development of a luciferase reporter gene, luxCt, for *Chlamydomonas reinhardtii* chloroplast," *The Plant Journal* (2004) 37:449-458.

McDonald et al., "Elevated extrahepatic expression and secretion of mammary-associated serum amyloid A 3 (M-SAA3) into colostrum," *Veterinary Immunology and Immunopathology* (2001) 83:203-211.

Chochet et al., "Translational regulations as specific traits of chloroplast gene expression", *FEBS Letter* (2002) (2006).

* cited by examiner

Bovine Serum Amyloid A3 in C. reinhardtii codon bias

```
C.r. ATG TGG GGT ACA TTC CTT AAA GAA GCT GGT CAA GGT GCT AAA GAC ATG TGG AGA GCT TAC
B.t. ATG TGG GGG ACA TTC CTC AAG GAA GCT GGT CAA GGG GCT AAA GAC ATG TGG AGA GCT TAC
      M   W   G   T   F   L   K   E   A   G   Q   G   A   K   D   M   W   R   A   Y

C.r. CAA GAC ATG AAA GAA GCT AAC TAC CGT GGT GCA GAC AAA TAC TTC CAC GCT CGT GGT AAC
B.t. CAA GAC ATG AAA GAA GCC AAC TAC AGG GGT GCA GAC AAA TAC TTC CAC GCC CGT GGA AAC
      Q   D   M   K   E   A   N   Y   R   G   A   D   K   Y   F   H   A   R   G   N

C.r. TAT GAC GCT GCT CGA CGT GGT CCT GGT GGT GCT TGG GCT GCT AAA GTA ATC AGT AAC GCT
B.t. TAT GAC GCT GCC CGA AGG GGA CCT GGG GGT GCC TGG GCT GCT AAA GTG ATC AGT AAC GCC
      Y   D   A   A   R   R   G   P   G   G   A   W   A   A   K   V   I   S   N   A

C.r. AGA GAA ACT ATT CAA GGT ATC ACA GAC CCT CTT TTT AAA GGT ATG ACA CGT GAC CAA GTA
B.t. AGA GAG ACT ATT CAG GGA ATC ACA GAC CCT CTG TTT AAG GGT ATG ACC AGG GAC CAG GTA
      R   E   T   I   Q   G   I   T   D   P   L   F   K   G   M   T   R   D   Q   V

C.r. CGT GAA GAT TCT AAA GCT GAC CAA TTT GCT AAC GAA TGG GGT CGT AGC GGT AAA GAC CCT
B.t. CGG GAG GAT TCG AAG GCC GAC CAG TTT GCC AAC GAA TGG GGC CGG AGC GGC AAA GAC CCC
      R   E   D   S   K   A   D   Q   F   A   N   E   W   G   R   S   G   K   D   P

C.r. AAC CAC TTC AGA CCT GCT GGT CTT CCT GAC AAA TAC TAA
B.t. AAC CAC TTC AGA CCT GCT GGC CTG CCT GAC AAA TAC TGA
      N   H   F   R   P   A   G   L   P   D   K   Y   *
```

FIG. 1

Accumulation of Bovine Serum Amyloid A3
in *C. reinhardtii* chloroplasts

Coomassie Stain       Anti-SAA3 Western

FIG. 4 psbA-M-SAA-rbcL-lux plasmid

FIG. 5

Expression of Bovine M-SAA3 driven by the psbA promoter and UTR

Coomassie stain gel | Western anti-SAA3

SEQUENCE LISTING

```
<160> NUMBER OF SEQ ID NOS: 12

<210> SEQ ID NO 1
<211> LENGTH: 348
<212> TYPE: DNA
<213> ORGANISM: Artificial sequence
<220> FEATURE:
<223> OTHER INFORMATION: Synthetic construct

<400> SEQUENCE: 1
catatgtggg gtacattcct taaagaagct ggtcaaggtg ctaaagacat gtggagagct      60
taccaagaca tgaaagaagc taactaccgt ggtgcagaca aatacttcca cgctcgtggt     120
aactatgacg ctgctcgacg tggtcctggt ggtgcttggg ctgctaaagt aatcagtaac     180
gctagagaaa ctattcaagg tatcacagac cctcttttta aaggtatgac acgtgaccaa     240
gtacgtgaag attctaaagc tgaccaattt gctaacgaat ggggtcgtag cggtaaagac     300
cctaaccact tcagacctgc tggtcttcct gacaaatact aatctaga                  348

<210> SEQ ID NO 2
<211> LENGTH: 112
<212> TYPE: PRT
<213> ORGANISM: Artificial sequence
<220> FEATURE:
<223> OTHER INFORMATION: Synthetic construct

<400> SEQUENCE: 2

Met Trp Gly Thr Phe Leu Lys Glu Ala Gly Gln Gly Ala Lys Asp Met
1               5                   10                  15

Trp Arg Ala Tyr Gln Asp Met Lys Glu Ala Asn Tyr Arg Gly Ala Asp
            20                  25                  30

Lys Tyr Phe His Ala Arg Gly Asn Tyr Asp Ala Ala Arg Arg Gly Pro
        35                  40                  45
```

Gly Gly Ala Trp Ala Ala Lys Val Ile Ser Asn Ala Arg Glu Thr Ile
         50                  55                  60

Gln Gly Ile Thr Asp Pro Leu Phe Lys Gly Met Thr Arg Asp Gln Val
 65                  70                  75                  80

Arg Glu Asp Ser Lys Ala Asp Gln Phe Ala Asn Glu Trp Gly Arg Ser
                 85                  90                  95

Gly Lys Asp Pro Asn His Phe Arg Pro Ala Gly Leu Pro Asp Lys Tyr
            100                 105                 110

<210> SEQ ID NO 3
<211> LENGTH: 1312
<212> TYPE: DNA
<213> ORGANISM: Artificial sequence
<220> FEATURE:
<223> OTHER INFORMATION: Synthetic construct

<400> SEQUENCE: 3
gaattccccc aagcccttcg ggcttgtatc ttttattatc taatggtaat aaaaaaagaa    60
gtgagtttat tcatttagta tttacaaagc tttatctcct cttacaggat taaaactcca   120
atatgctatt cccgaagggg tagggttaga aaaagaacgc cacaaagctg tagggtttcg   180
atttgctatc tccgaatctg ccaatcgccg tccccttccc ctaaccggac gccagtggca   240
atggtaccgc cactgccttc ttccccttcc ccggcaggac gttagtcgat atttatacac   300
tcttaagttt acttgcccaa tatttatatt aggacgtccc cttcgggtaa ataaatttta   360
gtggcagtgg taccaccact gcctatttta atactccgaa gcatataaat atacttcgga   420
gtatataaat atccactaat atttatatta ggcagttggc aggcaacaat aaataaattt   480
gtcccgtaag gggacgtccc gaaggggaag gggaagaagg cagttgcctc gcctatcggc   540
taacaagttc ctttggagta tataaccgcc tacaggtaac ttaaagaaca tttgttaccc   600
gtaggggttt atacttctaa ttgcttcttc tgaacaataa aatggtttgt gtggtctggg   660
ctaggaaact tgtaacaatg tgtagtgtcg cttccgcttc ccttcgggac gtccccttcg   720
ggtaagtaaa cttaggagta ttaaatcggg acgtccccct cgggtaaata aatttcagtg   780
gacgtcccct tacgggacgc cagtagacgt cagtggcagt tgcctcgcct atcggctaac   840
aagttccttc ggagtatata aatatagaat gtttacatac tcctaagttt acttgcctcc   900
ttcggagtat ataaatatcc gaaggggaa ggaggacgcc agtggcagtg gtaccgccac   960
tgcctgcttc ctccttcgga gtatgtaaac cccttcgggc aactaaagtt tatcgcagta  1020
tataaatata ggcagttggc aggcaactgc cactgacgtc ctattttaat actccgaagg  1080
aggcagttgg caggcaactg ccactgacgt cccgtaaggg taaggggacg tccactggcg  1140
tcccgtaagg ggaagggac gtaggtacat aaatgtgcta ggtaactaac gtttgatttt  1200 tgtggtata atatatgtac catgctttta atagaagctt gaattataa attaaaatat   1260 ttttacaata ttttacggag aaattaaaac tttaaaaaaa ttaacatatg ac           1312

<210> SEQ ID NO 4
<211> LENGTH: 1531
<212> TYPE: DNA
<213> ORGANISM: Artificial sequence
<220> FEATURE:
<223> OTHER INFORMATION: Synthetic construct

<400> SEQUENCE: 4
ttttttttta aactaaaata aatctggtta accataccctg gtttatttta gtttatacac    60

-continued

```
acttttcata tatatatact taatagctac cataggcagt tggcaggacg tcccccttacg      120 ggacaaatgt atttattgtt gcctgccaac tgcctaatat aaatattagt ggacgtcccc      180
ttccccttac gggcaagtaa acttagggat tttaatgctc cgttaggagg caaataaatt      240
ttagtggcag ttgcctcgcc tatcggctaa caagttcctt cggagtatat aaatatcctg      300
ccaactgccg atatttatat actaggcagt ggcggtacca ctcgactaat atttatattc      360
cgtaagacgt cctccttcgg agtatgtaaa catgctaagt ttacttgccc aatatttata      420
ttaggacgtc agtggcagtg gaccaccact cgtattttat actcgaaagg cagttggcag      480
gcaactcgac taaaatttat ttacccgaag acgtcccgaa gaaggggaag gaggcagtgg      540
taccaccact ggctccgcag tattaacatc ctatatttat atactccgaa gaacttctta      600
gccgatggca actgccacaa aaaccatcg gcttcgtttc acacagatgg tgagaaccac       660
acgtttcgtc ctataaaaat agctaagttt acttgcccaa tatttatatt aggacgtccc      720
cttcggtaaa taaattttag tggctgtgtg acgttcactg gcgtcttggt aggttctgtg      780
actgactaaa taaaaagta tttgtcgtct acgatatgta aatctgtcgt atacgatatg       840
taaatttgag ctcttatggc ctctacatcg aggtttatta tcttaccgaa ggtaaatgcc      900
ttcgtggatc ttatgggacg tcctgtgtcc ttcctagtgg tcaataatca cttcgtgaca      960
gcctgggctt acatttatat aagcgctgtt atatttatac gctgttagac aaggtttaaa     1020
tacataaatt tttattagtc tatcgaccgt taattgctta acttaccgaa ggttaatcgc     1080
tttacttacc gaaggttaat cgctttactt accgaaggtt aattgcttaa cttactgaag     1140
gttaatcgct ttacttaccg aaggttaatt gcttaactta ctgaaggtta atcgctttac     1200
ttaccgaagg ttaatccaat tttttttcg ccatatgtag acgtttaatt gctacaacgt      1260 tattagccttt cgtcgctat caaatcggtt cagatatata tcactttatt cactttcgtt     1320
tatattatgg ctggattagg tcttttagtt aattaaaatt tacatatttta atgctattta     1380 ttattattgc aattgcatta aatatttttt taaaaaaat taatcttcag ctatattagt      1440
aaataaccca taaatagttt caattggaat aattggaatt ggatatggac tagttttatt     1500
ttcttctaat aactttaata tcgctggatc c                                    1531
```

<210> SEQ ID NO 5
<211> LENGTH: 373
<212> TYPE: DNA
<213> ORGANISM: Artificial sequence
<220> FEATURE:
<223> OTHER INFORMATION: Synthetic construct

<400> SEQUENCE: 5

```
ggatccgtcg actggtaccg ccactgcctg cttcctcctt cggagtatgt aaaccccttc       60
gggcaactaa agtttatcgc agtatataaa tataggcagt tggcaggcaa ctgccactga      120
cgtcctattt taatactccg aaggaggcag ttggcaggca actgccactg acgtcccgta      180
agggtaaggg gacgtccact ggcgtcccgt aaggggaagg ggacgtaggt acataaatgt      240
gctaggtaac taacgtttga ttttttgtgg tataatatat gtaccatgct tttaatagaa      300
gcttgaattt ataaattaaa atatttttac aatatttac gagaaattaa aactttaaaa      360
aaattaacat atg                                                        373
```

<210> SEQ ID NO 6
<211> LENGTH: 468
<212> TYPE: DNA
<213> ORGANISM: Artificial sequence
<220> FEATURE:
<223> OTHER INFORMATION: Synthetic construct

<400> SEQUENCE: 6

```
ggatccctag taacggccgc cagtgtgctg gaatttgagt atatgaaatt aaatggatat      60
ttggtacatt taattccaca aaaatgtcca atacttaaaa tacaaaatta aaagtattag     120
ttgtaaactt gactaacatt ttaaatttta aatttttttcc taattatata ttttacttgc    180
aaaatttata aaaattttat gcattttttat atcataataa taaaacccttt attcatggtt  240
tataatataa taattgtgat gactatgcac aaagcagttc tagtcccata tataaacta     300
tatataaccc gtttaaagat ttatttaaaa atatgtgtgt aaaaaatgct tattttttaat   360
tttatttttat ataagttata atattaaata cacaatgatt aaaattaaat aataataaat   420
ttaacgtaac gatgagttgt tttttttattt tggagataca cgcatatg                468
```

<210> SEQ ID NO 7
<211> LENGTH: 2025
<212> TYPE: DNA
<213> ORGANISM: Artificial sequence
<220> FEATURE:
<223> OTHER INFORMATION: Synthetic construct

<400> SEQUENCE: 7

```
catatgaaac gtttagttaa tttaggtaaa gcttctgaag gttgtggttt cgacacagtt      60
tggttattag aacatcactt tactgaattt ggtttattag gtaacccctta tgttgctgct   120
gcacatctat taggtgctac agaaaaactt aatgttggta ctgctgctat tgtattacct   180
actgctcacc ctgttcgtca agcagaagac gtaaatttat tagatcaaat gtcaaaagga  240
cgttttcgtt ttggtatttg tcgtggttta tacgacaaag atttccgtgt ttttggtaca  300
gacatggata atagtcgtgc tttaatggac tgttggtatg acttaatgaa agaaggtttt  360
aacgaaggtt atattgctgc agataatgaa catattaaat tccctaaaat tcaattaaat  420
ccatcagctt acacacaagg tggtgctcct gtttatgttg ttgctgaatc agcatcaaca  480
acagaatggg ctgctgaacg tggtttacca atgattctaa gttggattat taatactcac  540
gaaaaaaaag cacatgttga tctttataat gaagttgcta ctgaacacgg ttacgatgta  600
actaaaattg accattgttt atcttatatt acttcagttg atcacgattc aaacaaagct  660
aaagatattt gtcgtaattt tttaggtcat tggtatgact catacgtaaa tgctacaaaa  720
attttttgatg actctgatca aacaaaaggt atgactttta taaaggtca atggcgtgat  780
tttgttttaa aaggtcacaa agatactaac cgtcgtattg attatagtta cgaaattaat  840
ccagtaggta cacctgaaga atgtatcgca attattcaac aagatatcga tgctacaggt  900
attaataata tttgttgtgg ttttgaagct aacggttctg aagaagaaat tatcgcttct  960
atgaaattat tcaatctgat gtaatgcca tatcttaaag aaaaacaatc tggtggtgga  1020
ggttcttcag gtggtggagg cggtggttct tcaaaatttg gattattttt ccttaatttt  1080
atgaattcaa aacgttcttc tgatcaagtt attgaagaaa tgttagatac tgcacattat  1140
gtagatcaat taaaatttga cacattagct gtttacgaaa atcactttttc aaacaatggt  1200
gtagttggtg ctccattaac agtagctggt tttttacttg gtatgacaaa aaacgctaaa  1260
gtagcttcat taaatcatgt tattactaca caccatccag tacgtgtagc tgaagaagca  1320
tgttacttg atcaaatgag tgaaggtcgt tttgttttttg gttttagtga ttgtgaaaaa  1380
agtgctgata tgcgtttttt taatcgtcca acagattctc aatttcaatt attcagtgaa  1440
```

```
tgtcacaaaa ttatcaatga tgcatttact actggttatt gtcatccaaa taatgatttt    1500
tacagttttc ctaaaatttc tgttaaccca cacgcttata ctgaaggtgg tcctgcacaa    1560
tttgtaaatg ctacaagtaa agaagtagtt gaatgggcag ctaaattagg tcttccactt    1620
gtatttaaat gggacgattc aaatgctcaa cgtaaagaat atgctggttt ataccatgaa    1680
gttgctcaag cacacggtgt tgatgttagt caagttcgtc ataaattaac actattagtt    1740
aatcaaaacg tagatggtga agcagctcgt gcagaagctc gtgtatattt agaagaattt    1800
gttcgtgaat cttatccaaa tactgacttt gaacaaaaaa tggtagaatt attatcagaa    1860
aacgctattg gtacttacga agaaagtact caagcagctc gtgttgcaat tgaatgttgt    1920
ggtgctgcag acttattaat gtcttttgaa tcaatggaag ataaagctca cgaacgtgca    1980
gttattgatg tagtaaatgc taacattgtt aaatatcatt cataa                    2025
```

<210> SEQ ID NO 8
<211> LENGTH: 673
<212> TYPE: PRT
<213> ORGANISM: Artificial sequence
<220> FEATURE:
<223> OTHER INFORMATION: Synthetic construct

<400> SEQUENCE: 8

```
Met Lys Arg Leu Val Asn Leu Gly Lys Ala Ser Glu Gly Cys Gly Phe
1               5                   10                  15

Asp Thr Val Trp Leu Glu His His Phe Thr Glu Phe Gly Leu Leu
                20                  25                  30

Gly Asn Pro Tyr Val Ala Ala His Leu Leu Gly Ala Thr Glu Lys
            35                  40                  45

Leu Asn Val Gly Thr Ala Ala Ile Val Leu Pro Thr Ala His Pro Val
    50                  55                  60

Arg Gln Ala Glu Asp Val Asn Leu Leu Asp Gln Met Ser Lys Gly Arg
65                  70                  75                  80

Phe Arg Phe Gly Ile Cys Arg Gly Leu Tyr Asp Lys Asp Phe Arg Val
                85                  90                  95

Phe Gly Thr Asp Met Asp Asn Ser Arg Ala Leu Met Asp Cys Trp Tyr
            100                 105                 110

Asp Leu Met Lys Glu Gly Phe Asn Glu Gly Tyr Ile Ala Ala Asp Asn
        115                 120                 125

Glu His Ile Lys Phe Pro Lys Ile Gln Leu Asn Pro Ser Ala Tyr Thr
    130                 135                 140

Gln Gly Gly Ala Pro Val Tyr Val Ala Glu Ser Ala Ser Thr Thr
145                 150                 155                 160

Glu Trp Ala Ala Glu Arg Gly Leu Pro Met Ile Leu Ser Trp Ile Ile
                165                 170                 175

Asn Thr His Glu Lys Lys Ala His Val Asp Leu Tyr Asn Glu Val Ala
            180                 185                 190

Thr Glu His Gly Tyr Asp Val Thr Lys Ile Asp His Cys Leu Ser Tyr
        195                 200                 205

Ile Thr Ser Val Asp His Asp Ser Asn Lys Ala Lys Asp Ile Cys Arg
    210                 215                 220

Asn Phe Leu Gly His Trp Tyr Asp Ser Tyr Val Asn Ala Thr Lys Ile
225                 230                 235                 240

Phe Asp Asp Ser Asp Gln Thr Lys Gly Tyr Asp Phe Asn Lys Gly Gln
                245                 250                 255

Trp Arg Asp Phe Val Leu Lys Gly His Lys Asp Thr Asn Arg Arg Ile
```

-continued

```
                260                 265                 270
Asp Tyr Ser Tyr Glu Ile Asn Pro Val Gly Thr Pro Glu Glu Cys Ile
            275                 280                 285
Ala Ile Ile Gln Gln Asp Ile Asp Ala Thr Gly Ile Asn Asn Ile Cys
290                 295                 300
Cys Gly Phe Glu Ala Asn Gly Ser Glu Glu Ile Ile Ala Ser Met
305                 310                 315                 320
Lys Leu Phe Gln Ser Asp Val Met Pro Tyr Leu Lys Glu Lys Gln Ser
            325                 330                 335
Gly Gly Gly Gly Ser Ser Gly Gly Gly Gly Ser Ser Lys Phe
            340                 345                 350
Gly Leu Phe Phe Leu Asn Phe Met Asn Ser Lys Arg Ser Ser Asp Gln
            355                 360                 365
Val Ile Glu Glu Met Leu Asp Thr Ala His Tyr Val Asp Gln Leu Lys
            370                 375                 380
Phe Asp Thr Leu Ala Val Tyr Glu Asn His Phe Ser Asn Asn Gly Val
385                 390                 395                 400
Val Gly Ala Pro Leu Thr Val Ala Gly Phe Leu Leu Gly Met Thr Lys
                405                 410                 415
Asn Ala Lys Val Ala Ser Leu Asn His Val Ile Thr Thr His His Pro
            420                 425                 430
Val Arg Val Ala Glu Glu Ala Cys Leu Leu Asp Gln Met Ser Glu Gly
            435                 440                 445
Arg Phe Val Phe Gly Phe Ser Asp Cys Glu Lys Ser Ala Asp Met Arg
            450                 455                 460
Phe Phe Asn Arg Pro Thr Asp Ser Gln Phe Gln Leu Phe Ser Glu Cys
465                 470                 475                 480
His Lys Ile Ile Asn Asp Ala Phe Thr Thr Gly Tyr Cys His Pro Asn
                485                 490                 495
Asn Asp Phe Tyr Ser Phe Pro Lys Ile Ser Val Asn Pro His Ala Tyr
            500                 505                 510
Thr Glu Gly Gly Pro Ala Gln Phe Val Asn Ala Thr Ser Lys Glu Val
            515                 520                 525
Val Glu Trp Ala Ala Lys Leu Gly Leu Pro Leu Val Phe Lys Trp Asp
            530                 535                 540
Asp Ser Asn Ala Gln Arg Lys Glu Tyr Ala Gly Leu Tyr His Glu Val
545                 550                 555                 560
Ala Gln Ala His Gly Val Asp Val Ser Gln Val Arg His Lys Leu Thr
                565                 570                 575
Leu Leu Val Asn Gln Asn Val Asp Gly Glu Ala Ala Arg Ala Glu Ala
            580                 585                 590
Arg Val Tyr Leu Glu Glu Phe Val Arg Glu Ser Tyr Pro Asn Thr Asp
            595                 600                 605
Phe Glu Gln Lys Met Val Glu Leu Leu Ser Glu Asn Ala Ile Gly Thr
            610                 615                 620
Tyr Glu Glu Ser Thr Gln Ala Ala Arg Val Ala Ile Glu Cys Cys Gly
625                 630                 635                 640
Ala Ala Asp Leu Leu Met Ser Phe Glu Ser Met Glu Asp Lys Ala His
                645                 650                 655
Glu Arg Ala Val Ile Asp Val Val Asn Ala Asn Ile Val Lys Tyr His
            660                 665                 670
Ser
```

```
<210> SEQ ID NO 9
<211> LENGTH: 339
<212> TYPE: DNA
<213> ORGANISM: Bovine

<400> SEQUENCE: 9
atgtggggga cattcctcaa ggaagctggt caagggcta aagacatgtg gagagcttac         60
caagacatga aagaagccaa ctacagggt gcagacaaat acttccacgc ccgtggaaac       120
tatgacgctg cccgaagggg acctgggggt gcctgggctg ctaaagtgat cagtaacgcc      180
agagagacta ttcagggaat cacagaccct ctgtttaagg gtatgaccag ggaccaggta      240
cgggaggatt cgaaggccga ccagtttgcc aacgaatggg gccggagcgg caaagacccc      300
aaccacttca gacctgctgg cctgcctgac aaatactga                              339

<210> SEQ ID NO 10
<211> LENGTH: 10
<212> TYPE: PRT
<213> ORGANISM: Artificial sequence
<220> FEATURE:
<223> OTHER INFORMATION: Synthetic construct

<400> SEQUENCE: 10

Arg Trp Gly Thr Phe Leu Lys Glu Ala Gly
1               5                   10

<210> SEQ ID NO 11
<211> LENGTH: 10
<212> TYPE: PRT
<213> ORGANISM: Artificial sequence
<220> FEATURE:
<223> OTHER INFORMATION: Synthetic construct

<400> SEQUENCE: 11

Gly Lys Phe Ala Trp Glu Gly Met Thr Leu
1               5                   10

<210> SEQ ID NO 12
<211> LENGTH: 10
<212> TYPE: PRT
<213> ORGANISM: Bovine

<400> SEQUENCE: 12

Met Trp Gly Thr Phe Leu Lys Glu Ala Gly
1               5                   10
```

ROBUST EXPRESSION OF A BIOACTIVE MAMMALIAN PROTEIN IN CHLAMYDOMONAS CHLOROPLAST

RELATED APPLICATIONS

This application claims the benefit of priority under 35 U.S.C. §119(e) of U.S. Provisional Application No. 60/779,120, filed May 9, 2006, and U.S. Provisional Application No. 60/903,692, filed Feb. 26, 2007, the contents of which are incorporated by reference in their entirety.

STATEMENT OF GOVERNMENT SUPPORT

This invention was made in part with government support under Grant Nos. RO1GM054659-08 and 5RO1 AI059614-02 awarded by the National Institutes of Health and DEFG0302ER15313 awarded by the Department of Energy. The government has certain rights in this invention.

BACKGROUND OF THE INVENTION

1. Field of the Invention

The present invention relates generally to methods and compositions for expressing polypeptides in plant cell chloroplasts, and more specifically to chimeric constructs that allow for expression of a gene of interest in algae.

2. Background Information

Protein based therapeutics, or biologics, are the fastest growing sector of drug development, mainly due to the efficacy and specificity of these molecules. The specificity of biologics comes from their complexity, and biologics are only produced in living cells, making the production of these molecules time consuming and expensive. The expression of biologics in *C. reinhardtii* offers an attractive alternative to traditional mammalian-based expression systems, as the production of proteins in algae has inherently low costs of capitalization and production, and stable transgenic lines can be generated in a short period of time.

Recombinant technologies have allowed for the rapid identification of proteins capable of providing an array of therapeutic functions, and the utility of these types of molecules continues to grow as more sophisticated molecules and approaches are developed. As protein identification and engineering techniques have advanced, the need for more efficient and rapid production systems has emerged as a limiting factor in therapeutic protein production. A key consideration in the development of any new protein based drug is the inherent high cost of goods and capital investment associated with the production of these molecules.

Currently, there are a number of protein expression systems available for the production of biologics, and each system has different characteristics in terms of protein yield, ease of manipulation, and cost of goods. The majority of therapeutic proteins produced today come from the culture of transgenic Chinese Hamster Ovary (CHO) cells. Due to high capital and media costs, and the inherent complexity of CHO production systems, proteins produced in this manner are very expensive. *E. coli* is also used for biologic production, and bacterial expression is much faster and cheaper than CHO production, but bacteria are inefficient at producing properly folded complex proteins, and also show poor yields of many complex proteins.

Recently terrestrial plants have been used for biologic production. In plant systems, the therapeutic protein is synthesized within the plant cells and deposited into leaf or seed tissues. A variety of biologics have been produced in plants, including complex antibodies such as dimeric secretory immunoglobulin A molecules (sIgA). Protein production in plants is inherently less expensive than production by cell fermentation, but there are two major drawbacks to this approach. First, the length of time required from the initial transformation event to having usable (mg to gram) quantities of a protein can take up to two years for crops such as tobacco, and over three years for species such as corn. A second concern surrounding the expression of human therapeutics in crop plants is the potential for gene flow (via pollen) to surrounding food crops, and for the contamination of food supplies with transgenic seeds expressing human therapeutic proteins.

Compared to land plants, algae like *C. reinhardtii* grow much faster, doubling in approximately 8 hours. As *C. reinhardtii* propagates by cell division, the time from initial transformation to protein production is significantly reduced relative to higher plants or mammalian cells, requiring as little as three weeks to generate stable transgenic lines, with the potential to scale up to production volumes in another four to six weeks. Algae propagate by vegetative replication, lack pollen, and have no potential for gene transfer to food crops. *C. reinhardtii* can easily be grown in containment, again reducing any chance of environmental contamination. Growth in containment also assures that external contaminants, like pesticides or pollutants, do not contaminate the protein being produced. Algae are eukaryotes, meaning that unlike bacteria, they are efficient at producing complex proteins and have the machinery necessary to fold and assemble multi-component complexes into functional proteins. In addition, green algae are generally regarded as safe (GRAS), posing little risk of viral, prion or bacterial endotoxin contamination. Thus, algae would seem to be an ideal system for biologic production, as long as high levels of protein expression can be achieved, and that the expressed protein can be shown to function in a bioactive manner.

SUMMARY OF THE INVENTION

The present invention discloses a method to achieve robust expression of exogenous gene products by direct replacement of an endogenous chloroplast gene, thereby eliminating competition or autoregulation of a transgene by the endogenous gene or protein. As such, the method is applicable to any chloroplast gene. The invention also discloses the construction of chimeric cassettes having various combinations of cognate and non-cognate promoter/UTR modules, including mutations therein, to effectively control gene expression.

In one embodiment, a method of expressing a gene is disclosed including transforming an algae cell by replacing an endogenous chloroplast gene via integration of a chimeric construct having a heterologous coding sequence, a promoter sequence, and at least one UTR, where the promoter is cognate or non-cognate to the endogenous chloroplast gene, and cultivating the transformed algae cell under conditions to allow expression of the gene. In one aspect, the endogenous chloroplast gene encodes a photosystem II (PSII) reaction center protein.

In another aspect, the heterologous coding sequence is driven by a non-cognate promoter to the replaced endogenous chloroplast gene and the chimeric construct comprises at least one non-cognate UTR to the endogenous chloroplast gene.

In one aspect, the replaced endogenous gene is re-inserted at a silent distal site and is driven by a cognate or non-cognate promoter. In a related aspect, when the chimeric construct and the inserted distal endogenous gene are driven by the cognate promoter, the gene product of the heterologous coding sequence is repressed. In another related aspect, when the chimeric construct is driven by the cognate promoter, a gene product encoded by the heterologous coding sequence is not repressed, and may be modulated by light. In another aspect, a gene product encoded by the heterologous coding sequence is constitutively expressed.

In one aspect, an algae cell transformed by such a method is disclosed.

In another embodiment, an algae extract is disclosed which is obtained from an algae cell transformed by replacing an endogenous chloroplast gene via integration of a chimeric construct having a heterologous coding sequence, a promoter sequence, and at least one UTR, wherein the promoter is cognate or non-cognate to the endogenous chloroplast gene.

In one aspect, a peptide expressed in the algae is approximately 0.25% to about 6% of the total protein in the extract.

In another embodiment, a method of treating intestinal bacterial or viral infection is disclosed, including administering to a subject in need thereof a therapeutically effective amount of an algae obtained from an algae cell transformed by replacing an endogenous chloroplast gene via integration of a chimeric construct having a heterologous coding sequence, a promoter sequence, and at least one UTR, wherein the promoter is cognate or non-cognate to the endogenous chloroplast gene.

In a related aspect, the subject, is a mammalian newborn or an infant, including, but not limited to humans, bovine, and porcine species.

In one embodiment, a chimeric construct is disclosed including a photosystem II (PSII) reaction center protein gene promoter, PSII gene 5' UTR, a multiple cloning site (MCS), and a PSII gene 3' UTR, having the configuration:

PSII gene promoter-PSII gene 5' UTR-MCS-PSII gene 3' UTR.

In one aspect, the PSII gene UTRs are from different PSII genes. In another aspect, the PSII gene promoter is a psbA or psbD promoter. In a related aspect, the MCS includes a gene encoding an amino acid sequence as set forth in SEQ ID NO:2.

In one embodiment, a method of expressing mammary associated serum amyloid A3 (M-SAA) is disclosed including, transforming an algae cell by replacing an endogenous chloroplast gene via integration of a chimeric construct having a heterologous coding sequence encoding SAA, a promoter sequence, and at least one UTR, wherein the promoter is cognate or non-cognate to the endogenous chloroplast gene; and cultivating the transformed algae cell under conditions to allow for expression of the transgene.

BRIEF DESCRIPTION OF THE DRAWINGS

FIG. 1 shows a comparison of the bovine M-SAA3 native sequence and codon optimized M-SAA3 coding regions. (SEQ ID NO'S 1 & 9). The amino acid sequence (SEQ ID NO:2) is shown with the modified codons indicated by boxed and shaded amino acids. The optimized codons were defined as codons used more than 10 times per 1000 codons in the *C. reinhardtii* chloroplast genome (Nakamura et al. 1999). The amino acid coding differences between the two proteins are indicated by boxed and unshaded amino acids.

FIG. 4 shows the detection of chloroplast expressed M-SAA3 proteins in transgenic psbD-M-SAA *C. reinhardtii* strains. Ten 10 μg of total soluble protein, from wt and M-SAA3 transgenic lines 1 and 7, was separated on 18% SDS PAGE and stained with Coomassie blue (left panel), or blotted to nitrocellulose membranes and decorated with anti-SAA antibody (right panel). M-SAA3 protein was visualized on Western blots by alkaline phosphatase activity staining.

FIG. 5 shows a map of psbA-M-SAA gene replacement vector used for expression in *C. reinhardtii* chloroplasts. Relevant restriction sites delineate the psbA promoter and 5' UTR (EcoR1/Nde I), the M-SAA3 coding region (NdeI/Xba I), and the psbA 3' UTR (Xba I/BamH I). Down stream of the SAA gene a luciferase gene, driven by the rbcL promoter, was inserted to follow gene integration into the psbA locus. The map shows the homologous genomic flanking region between plasmid psbA-M-SAA-rbcL-lux and the *C. reinhardtii* chloroplast genome into which the chimeric psbA-M-SAA gene was inserted.

FIG. 8 shows the detection of chloroplast expressed M-SAA3 proteins in transgenic psbA-M-SAA *C. reinhardtii* strains. Ten 10 μg of total soluble protein, from wt and psbA-M-SAA3 transgenic lines 1 and 22, was separated on 18% SDS PAGE and stained with Coomassie blue (left panel), or blotted to nitrocellulose membranes and decorated with anti-SAA antibody (right panel). M-SAA3 protein was visualized on Western blots by alkaline phosphatase activity staining. The figure also illustrates that SAA predominantly accumulates in the soluble phase of chloroplasts. Proteins from strain SAA-22 were separated into soluble (Sol) and non-soluble (Memo) fractions and either stained with Compassion blue (left panel) or blotted and hybridized with anti-SAA antisera (right panel).

FIG. 9 shows a map of psbA (D1) coding region replacement vectors. A). Relevant restriction sites delineate the truncated psbA promoter and 5' UTR (Bam/Nde I), the D1 coding region (NdeI/Xba I) and the psbA 3' UTR (Xba I/BamH I). The truncated D1 gene was ligated into the Bam site of transformation vector p3HB for introduction into the chloroplast genome near the psbH gene. B). Relevant restriction sites delineate the truncated D2 (psbD) promoter and 5'UTR (Bam/Nde I), the D1 coding region (NdeI/Xba I) and the psbA 3' UTR (Xba I/BamH I). The truncated D2-D1 chimeric gene was ligated into the Bam site of transformation vector p3HB for introduction into the chloroplast genome near the psbH gene.

DETAILED DESCRIPTION OF THE INVENTION

Figure 2:
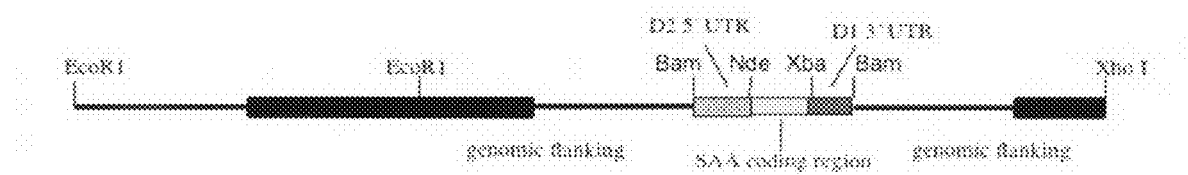
FIG. 2 illustrates a map of psbD-M-SAA3 genes used for expression in *C. reinhardtii* chloroplasts. Relevant restriction sites delineate the psbD 5' UTR (Bam/Nde I), the M-SAA3 coding region (NdeI/Xba I) and the psbA 3' UTR (Xba I/BamH I). The map shows the homologous genomic flanking regions between plasmid p322 and the *C. reinhardtii* chloroplast genome into which the chimeric psbD-M-SAA3 gene was inserted. *C. reinhardtii* chloroplast DNA depicted is the EcoR I to Xho I fragment located in the inverted repeat region of the chloroplast genome. Regions corresponding to the probes used in the Southern and Northern blot analysis are the SAA coding region and the Bam to Xho genomic flanking region. Black boxes indicate, from I to r, psbA and ribosomal RNA genes, respectively.

Before the present composition, methods, and treatment methodology are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As used herein "cognate" is used in a comparative sense to refer to genetic elements that are typically associated with a specific reference gene. For example, for the PSII gene psbA (i.e., a specific reference gene), cognate genetic elements would include, but are not limited to, a psbA promoter, psbA 5' UTR, and psbA 3' UTR. Contrapositively, "non-cognate" would refer to genetic elements that are not typically related to a specific reference gene. For example, but not limited to, where a chimeric construct comprising a psbA promoter and psbD 5' UTR is to be homologously recombined at a psbA site, the 5' UTR in the construct would be non-cognate to psbA.

As used herein "transgene" means any gene carried by a vector or vehicle, where the vector or vehicle includes, but is not limited to, plasmids and viral vectors.

In a related aspect, integration of chimeric constructs into plastid genomes includes homologous recombination. In a further related aspect, cells transformed by the methods of the present invention may be homoplasmic or heteroplasmic for the integration, wherein homoplastic means all copies of the transformed plastid genome carry the same chimeric construct.

As used herein, the term "modulate" refers to a qualitative or quantitative increase or decrease in the amount of an expressed gene product. For example, where the use of light increases or decreases the measured amount of protein or RNA expressed by a cell, such light modulates the expression of that protein or RNA. In one aspect, modulation of expression includes autoregulation, where "autoregulation" refers to processes that maintain a generally constant physiological state in a cell or organism, and includes autorepression and autoinduction.

In a related aspect, autorepression is a process by which excess endogenous protein or endogenous mRNA results in decreasing the amount of expression of that endogenous protein. In a further related aspect, reduction of endogenous protein synthesis will result in increased transgene expression. In one aspect, operatively linking non-cognate genetic elements (e.g., promoters) to the endogenous gene is used to drive low levels of endogenous protein expression. In another aspect, mutations are introduced into the endogenous gene sequence and/or cognate genetic elements to reduce expression of the endogenous protein.

As used herein, the term "multiple cloning site" is used broadly to refer to any nucleotide or nucleotide sequence that facilitates linkage of a first polynucleotide to a second polynucleotide. Generally, a cloning site comprises one or a plurality restriction endonuclease recognition sites, for example, a cloning site, or one or a plurality of recombinase recognition sites, for example, a loxP site or an att site, or a combination of such sites. The cloning site can be provided to facilitate insertion or linkage, which can be operative linkage, of the first and second polynucleotide, for example, a first polynucleotide encoding a first 5' UTR operatively linked to second polynucleotide comprising a homologous coding sequence encoding a polypeptide of interest, linked to a first 3' UTR, which is to be translated in a prokaryote or a chloroplast or both.

In one embodiment, a chimeric construct is disclosed including a photosystem II (PSII) reaction center protein gene promoter, PSII gene 5' UTR, a multiple cloning site (MCS), and a PSII gene 3' UTR, having the configuration:

PSII gene promoter-PSII gene 5' UTR-MCS-PSII gene 3' UTR.

In a related aspect, the PSII gene UTRs are from different PSII genes and my include, but are not limited to, a psbD 5' UTR and a psbA 5' UTR.

In another related aspect, the PSII gene promoter is a psbA or psbD promoter and the 3' UTR is a psbA 3' UTR.

In one aspect, the MCS comprises a gene encoding the amino acid sequence as set forth in SEQ ID NO:2.

In one aspect, the PSII gene promoter and PSII gene 5' UTR are from psbD. In another aspect, the PSII gene 3' UTR is a psbA 3' UTR.

As used herein, the term "photosystem II reaction center" refers to an intrinsic membrane-protein complex in the chloroplast made of D1 (psbA gene), D2 (psbD gene), alpha and beta subunits of cytochrome b-559 (psbE and psbF genes respectively), the psbI gene product and a few low molecular weight proteins (e.g., 9 kDa peptide [psbH gene] and 6.5 kDa peptide [psb W gene]). In a related aspect, endogenous genes embrace chloroplast genes that exhibit autoregulation of translation, and include, but are not limited to, cytochrome f (i.e., C-terminal domain) and photosystem I reaction center genes (e.g., psaA, PsaB, PsaC, PsaJ).

As used herein, the term "operatively linked" means that two or more molecules are positioned with respect to each other such that they act as a single unit and effect a function attributable to one or both molecules or a combination thereof. For example, a polynucleotide encoding a polypeptide can be operatively linked to a transcriptional or translational regulatory element, in which case the element confers its regulatory effect on the polynucleotide similarly to the way in which the regulatory element would effect a polynucleotide sequence with which it normally is associated with in a cell.

The term "polynucleotide" or "nucleotide sequence" or "nucleic acid molecule" is used broadly herein to mean a sequence of two or more deoxyribonucleotides or ribonucleotides that are linked together by a phosphodiester bond. As such, the terms include RNA and DNA, which can be a gene or a portion thereof, a cDNA, a synthetic polydeoxyribonucleic acid sequence, or the like, and can be single stranded or double stranded, as well as a DNA/RNA hybrid. Furthermore, the terms as used herein include naturally occurring nucleic acid molecules, which can be isolated from a cell, as well as synthetic polynucleotides, which can be prepared, for example, by methods of chemical synthesis or by enzymatic methods such as by the polymerase chain reaction (PCR). It should be recognized that the different terms are used only for convenience of discussion so as to distinguish, for example, different components of a composition, except that the term "synthetic polynucleotide" as used herein refers to a polynucleotide that has been modified to reflect chloroplast codon usage.

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. Depending on the use, however, a polynucleotide also can contain nucleotide analogs, including non-naturally occurring synthetic nucleotides or modified naturally occurring nucleotides. Nucleotide analogs are well known in the art and commercially available (e.g., Ambion, Inc.; Austin Tex.), as are polynucleotides containing such nucleotide analogs (Lin et al., Nucl. Acids Res. 22:5220-5234, 1994; Jellinek et al., Biochemistry 34:11363-11372, 1995; Pagratis et al., Nature Biotechnol. 15:68-73, 1997). The covalent bond linking the nucleotides of a polynucleotide generally is a phosphodiester bond. However, depending on the purpose for which the polynucleotide is to be used, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., Nucl. Acids Res. 22:977-986, 1994; Ecker and Crooke, BioTechnology 13:351360, 1995).

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

The term "recombinant nucleic acid molecule" is used herein to refer to a polynucleotide that is manipulated by human intervention. A recombinant nucleic acid molecule can contain two or more nucleotide sequences that are linked in a manner such that the product is not found in a cell in nature. In particular, the two or more nucleotide sequences can be operatively linked and, for example, can encode a fusion polypeptide, or can comprise an encoding nucleotide sequence and a regulatory element, particularly a PSII promoter operatively linked to a PSII 5' UTR. A recombinant nucleic acid molecule also can be based on, but manipulated so as to be different, from a naturally occurring polynucleotide, for example, a polynucleotide having one or more nucleotide changes such that a first codon, which normally is found in the polynucleotide, is biased for chloroplast codon usage, or such that a sequence of interest is introduced into the polynucleotide, for example, a restriction endonuclease recognition site or a splice site, a promoter, a DNA origin of replication, or the like.

One or more codons of an encoding polynucleotide can be biased to reflect chloroplast codon usage. Most amino acids are encoded by two or more different (degenerate) codons, and it is well recognized that various organisms utilize certain codons in preference to others. Such preferential codon usage, which also is utilized in chloroplasts, is referred to herein as "chloroplast codon usage". Table 1 (below) shows the chloroplast codon usage for *C. reinhardtii*.

TABLE 1

Chloroplast Codon Usage in *Chlamydomonas reinhardtii*

| | | | |
|---|---|---|---|
| UUU 34.1*(348**) | UCU 19.4(198) | UAU 23.7(242) | UGU 8.5(87) |
| UUC 14.2(145) | UCC 4.9(50) | UAC 10.4(106) | UGC 2.6(27) |
| UUA 72.8(742) | UCA 20.4(208) | UAA 2.7(28) | UGA 0.1(1) |
| UUG 5.6(57) | UCG 5.2(53) | UAG 0.7(7) | UGG 13.7(140) |
| CUU 14.8(151) | CCU 14.9(152) | CAU 11.1(113) | CGU 25.5(260) |
| CUC 1.0(10) | CCC 5.4(55) | CAC 8.4(86) | CGC 5.1(52) |
| CUA 6.8(69) | CCA 19.3(197) | CAA 34.8(355) | CGA 3.8(39) |
| CUG 7.2(73) | CCG 3.0(31) | CAG 5.4(55) | CGG 0.5(5) |
| AUU 44.6(455) | ACU 23.3(237) | AAU 44.0(449) | AGU 16.9(172) |
| AUC 9.7(99) | ACC 7.8(80) | AAC 19.7(201) | AGC 6.7(68) |
| AUA 8.2(84) | ACA 29.3(299) | AAA 61.5(627) | AGA 5.0(51) |
| AUG 23.3(238) | ACG 4.2(43) | AAG 11.0(112) | AGG 1.5(15) |
| GUU 27.5(280) | GCU 30.6(312) | GAU 23.8(243) | GGU 40.0(408) |
| GUC 4.6(47) | GCC 11.1(113) | GAC 11.6(118) | GGC 8.7(89) |
| GUA 26.4(269) | GCA 19.9(203) | GAA 40.3(411) | GGA 9.6(98) |
| GUG 7.1(72) | GCG 4.3(44) | GAG 6.9(70) | GGG 4.3(44) |

*Frequency of codon usage per 1,000 codons.
**Number of times observed in 36 chloroplast coding sequences (10,193 codons).

The term "biased", when used in reference to a codon, means that the sequence of a codon in a polynucleotide has been changed such that the codon is one that is used preferentially in chloroplasts (see Table 1). A polynucleotide that is biased for chloroplast codon usage can be synthesized de novo, or can be genetically modified using routine recombinant DNA techniques, for example, by a site directed mutagenesis method, to change one or more codons such that they are biased for chloroplast codon usage. As disclosed herein, chloroplast codon bias can be variously skewed in different plants, including, for example, in alga chloroplasts as compared to tobacco.

Table 1 exemplifies codons that are preferentially used in alga chloroplast genes. The term "chloroplast codon usage" is used herein to refer to such codons, and is used in a comparative sense with respect to degenerate codons that encode the same amino acid but are less likely to be found as a codon in a chloroplast gene. The term "biased", when used in reference to chloroplast codon usage, refers to the manipulation of a polynucleotide such that one or more nucleotides of one or more codons is changed, resulting in a codon that is preferentially used in chloroplasts. Chloroplast codon bias is exemplified herein by the alga chloroplast codon bias as set forth in Table 1. The chloroplast codon bias can, but need not, be selected based on a particular plant in which a synthetic polynucleotide is to be expressed. The manipulation can be a change to a codon, for example, by a method such as site directed mutagenesis, by a method such as PCR using a primer that is mismatched for the nucleotide(s) to be changed such that the amplification product is biased to reflect chloroplast codon usage, or can be the de novo synthesis of polynucleotide sequence such that the change (bias) is introduced as a consequence of the synthesis procedure.

In addition to utilizing chloroplast codon bias as a means to provide efficient translation of a polypeptide, it will be recognized that an alternative means for obtaining efficient translation of a polypeptide in a chloroplast to re-engineer the chloroplast genome (e.g., a *C. reinhardtii* chloroplast genome) for the expression of tRNAs not otherwise expressed in the chloroplast genome. Such an engineered algae expressing one or more heterologous tRNA molecules provides the advantage that it would obviate a requirement to modify every polynucleotide of interest that is to be introduced into and expressed from a chloroplast genome; instead, algae such as *C. reinhardtii* that comprise a genetically modified chloroplast genome can be provided and utilized for efficient translation of a polypeptide according to a method of the invention. Correlations between tRNA abundance and codon usage in highly expressed genes is well known (Franklin et al., Plant J. 30:733-744, 2002; Dong et al., J. Mol. Biol. 260:649-663, 1996; Duret, Trends Genet. 16:287-289, 2000; Goldman et. al., J. Mol. Biol. 245:467-473, 1995; Komar et. al., Biol. Chem. 379:1295-1300, 1998). In *E. coli*, for example, re-engineering of strains to express underutilized tRNAs resulted in enhanced expression of genes which utilize these codons (see Novy et al., in Novations 12:1-3, 2001). Utilizing endogenous tRNA genes, site directed mutagenesis can be used to make a synthetic tRNA gene, which can be introduced into chloroplasts to complement rare or unused tRNA genes in a chloroplast genome such as a *C. reinhardtii* chloroplast genome.

Generally, the chloroplast codon bias selected for purposes of the present invention, including, for example, in preparing a synthetic polynucleotide as disclosed herein reflects chloroplast codon usage of a plant chloroplast, and includes a codon bias that, with respect to the third position of a codon, is skewed towards A/T, fore example, where the third position has greater than about 66% AT bias, particularly greater than about 70% AT bias. As such, chloroplast codon biased for purposes of the present invention excludes the third position bias observed, for example, in *Nicotiana tabacus* (tobacco), which has 34.56% GC bias in the third codon position (Morton B R, J Mol Evol (1993) 37(3):273-80). In one embodiment, the chloroplast codon usage is biased to reflect alga chloroplast codon usage, for example, *C. reinhardtii*, which has about 74.6% AT bias in the third codon position.

In one embodiment, a method to produce functional polypeptides/proteins is disclosed. The term "functional polypeptides/protein" is used broadly to refer to macromolecules comprising linear polymers of amino acids which act in biological systems, for example, as structural components, enzymes, chemical messengers, receptors, ligands, regulators, hormones, and the like. In one aspect, the functional polypeptides/proteins would include gut activate proteins including, but not limited to, serum amyloid A3, immunoglobulins, K-casein, lysozyme, lactoferrin, haptocorrin, a-lactalbumin, and lactoperoxidase, and the like (e.g., human milk proteins), where such proteins are relatively resistant against proteolysis in the gastrointestinal tract and may, in intact or partially digested form, contribute to the defense against pathogenic bacteria and viruses. In another aspect, such functional polypeptides/protein would include hormones, cytokines, or other active proteins and may be expressed separately or as a fusion protein comprising a separate protein capable of crossing the gut (e.g., transferin).

In another aspect, such polypeptides/proteins would include functional protein complexes, such as antibodies. The term "antibody" is used broadly herein to refer to a polypeptide or a protein complex that can specifically bind an epitope of an antigen. Generally, an antibody contains at least one antigen binding domain that is formed by an association of a heavy chain variable region domain and a light chain variable region domain, particularly the hypervariable regions. An antibody generated according to a method of the invention can be based on naturally occurring antibodies, for example, bivalent antibodies, which contain two antigen binding domains formed by first heavy and light chain variable regions and second heavy and light chain variable regions (e.g., an IgG or IgA isotype) or by a first heavy chain variable region and a second heavy chain variable region ($V_{HH}$ antibodies; see, for example, U.S. Pat. No. 6,005,079), or on non-naturally occurring antibodies, including, for example, single chain antibodies, chimeric antibodies, bifunctional antibodies, and humanized antibodies, as well as antigen-binding fragments of an antibody, for example, an Fab fragment, an Fd fragment, an Fv fragment, and the like. In a related aspect, a heterologous gene encodes a single chain antibody comprising a heavy chain operatively linked to a light chain.

In another related aspect, polynucleotides useful for practicing a method of the producing such antibodies can be isolated from cells producing the antibodies of interest, for example, B cells from an immunized subject or from an individual exposed to a particular antigen, can be synthesized de novo using well known methods of polynucleotide synthesis, can be produced recombinantly or can be obtained, for example, by screening combinatorial libraries of polynucleotides that encode variable heavy chains and variable light chains (see Huse et al., Science 246:1275-1281 (1989)), and can be biased for chloroplast codon usage, if desired (see Table 1). These and other methods of making polynucleotides encoding, for example, chimeric, humanized, CDR-grafted, single chain, and bifunctional antibodies are well known to those skilled in the art (Winter and Harris, Immunol. Today 14:243-246, 1993; Ward et al., Nature 341:544-546, 1989; Harlow and Lane, Antibodies: A laboratory manual (Cold Spring Harbor Laboratory Press, 1988); Hilyard et al., Protein Engineering: A practical approach (IRL Press 1992); Borrabeck, Antibody Engineering, 2d ed. (Oxford University Press 1995)).

Polynucleotides encoding humanized monoclonal antibodies, for example, can be obtained by transferring nucleotide sequences encoding mouse complementarity determining regions (CDRs) from heavy and light variable chains of the mouse immunoglobulin gene into a human variable domain gene, and then substituting human residues in the framework regions of the murine counterparts. General techniques for cloning murine immunoglobulin variable domains are known (see, for example, Orlandi et al., Proc. Natl. Acad. Sci., USA 86:3833, 1989), as are methods for producing humanized monoclonal antibodies (see, for example, Jones et al., Nature 321:522, 1986; Riechmann et al., Nature 332:323, 1988; Verhoeyen et al., Science 239:1534, 1988; Carter et al., Proc. Natl. Acad. Sci., USA 89:4285, 1992; Sandhu, Crit. Rev. Biotechnol. 12:437, 1992; and Singer et al., J. Immunol. 150:2844, 1993).

The disclosed methods can also be practiced using polynucleotides encoding human antibody fragments isolated from a combinatoria immunoglobulin library (see, for example, Barbas et al., Methods: A Companion to Methods in Immunology 2:119, 1991; Winter et al., Ann. Rev. Immunol. 12:433, 1994). Cloning and expression vectors that are useful for producing a human immunoglobulin phage library can be obtained, for example, from Stratagene Cloning Systems (La Jolla, Calif.).

A polynucleotide encoding a human monoclonal antibody also can be obtained, for example, from transgenic mice that have been engineered to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas, from which polynucleotides useful for practicing a method of the invention can be obtained. Methods for obtaining human antibodies from transgenic mice are described, for example, by Green et al., Nature Genet. 7:13, 1994; Lonberg et al., Nature 368:856, 1994; and Taylor et al., Intl. Immunol. 6:579, 1994, and such transgenic mice are commercially available (Abgenix, Inc.; Fremont Calif.).

The polynucleotide also can be one encoding an antigen binding fragment of an antibody. Antigen binding antibody fragments, which include, for example, Fv, Fab, Fab', Fd, and $F(ab')_2$ fragments, are well known in the art, and were originally identified by proteolytic hydrolysis of antibodies. For example, antibody fragments can be obtained by pepsin or papain digestion of whole antibodies by conventional methods. Antibody fragments produced by enzymatic cleavage of antibodies with pepsin generate a 5S fragment denoted $F(ab')_2$. This fragment can be further cleaved using a thiol reducing agent and, optionally, a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see, for example, Goldenberg, U.S. Pat. No. 4,036,945 and U.S. Pat. No. 4,331, 647, and references contained therein; Nisonhoff et al., Arch. Biochem. Biophys. 89:230. 1960; Porter, Biochem. J. 73:119, 1959; Edelman et al., Meth. Enzymol. 1:422 (Academic Press 1967); Coligan et al., In Curr. Protocols Immunol., 1992, see sections 2.8.1-2.8.10 and 2.10.1-2.10.4).

Another form of an antibody fragment is a peptide coding for a single complementarity-determining region (CDR). CDR peptides can be obtained by constructing a polynucleotide encoding the CDR of an antibody of interest, for example, by using the polymerase chain reaction to synthesize the variable region from RNA of antibody-producing cells (see, for example, Larrick et al., Methods: A Companion to Methods in Enzymology 2:106, 1991). Polynucleotides encoding such antibody fragments, including subunits of such fragments and peptide linkers joining, for example, a heavy chain variable region and light chain variable region, can be prepared by chemical synthesis methods or using routine recombinant DNA methods, beginning with polynucleotides encoding full length heavy chains and light chains, which can be obtained as described above.

Single celled alga, like C. reinhardtii, are essentially water borne plants and as such can produce proteins in a very cost effective manner. In addition, algae can be grown in complete containment, and there are a number of companies around the world that have develop large scale production of algae as human nutraceuticals or as a food source for farmed fish and other organisms. Capitalization costs for an algal production facility is also much less costly than for other types of cell culture, mainly because of the nature of algae and it's ability to grow with minimal input, using $CO_2$ as a carbon source and sunlight as an energy source. Although in many ways algae are an ideal system for therapeutic protein production there are a number of technical challenges that need to be met before algae can be used as an efficient production platform. Among these challenges are developing vectors that allow for consistent high levels of protein expression.

A recombinant nucleic acid molecule useful in a method of the invention can be contained in a vector. The vector can be any vector useful for introducing a polynucleotide into a chloroplast and, preferably, includes a nucleotide sequence of chloroplast genomic DNA that is sufficient to undergo homologous recombination with chloroplast genomic DNA, for example, a nucleotide sequence comprising about 400 to 1500 or more substantially contiguous nucleotides of chloroplast genomic DNA. Chloroplast vectors and methods for selecting regions of a chloroplast genome for use as a vector are well known (see, for example, Bock, J. Mol. Biol. 312: 425-438, 2001; see, also, Staub and Maliga, Plant Cell 4:39-45, 1992; Kavanagh et al., Genetics 152:1111-1122, 1999).

The entire chloroplast genome of C. reinhardtii has been sequenced (Maul et al., Plant Cell (2002) 14(11):2659-79; GenBank Acc. No. BK000554). Generally, the nucleotide sequence of the chloroplast genomic DNA is selected such that it is not a portion of a gene, including a regulatory sequence or coding sequence, particularly a gene that, if disrupted due to the homologous recombination event, would produce a deleterious effect with respect to the chloroplast, for example, for replication of the chloroplast genome, or to a plant cell containing the chloroplast. In this respect, the Accession No. disclosing the C. reinhardtii chloroplast genome sequence also provides maps showing coding and non-coding regions of the chloroplast genome, thus facilitating selection of a sequence useful for constructing a vector of the invention. For example, the chloroplast vector, p322, which is used in experiments disclosed herein, is a clone extending from the Eco (Eco RI) site at about position 143.1 kb to the Xho (Xho I) site at about position 148.5 kb.

The vector also can contain any additional nucleotide sequences that facilitate use or manipulation of the vector, for example, one or more transcriptional regulatory elements, a sequence encoding a selectable markers, one or more cloning sites, and the like. In one embodiment, the chloroplast vector contains a prokaryote origin of replication (ori), for example, an E. coli ori, thus providing a shuttle vector that can be passaged and manipulated in a prokaryote host cell as well as in a chloroplast.

The methods of the present invention are exemplified using the microalga, C. reinhardtii. The use of microalgae to express a polypeptide or protein complex according to a method of the invention provides the advantage that large populations of the microalgae can be grown, including commercially (Cyanotech Corp.; Kailua-Kona Hi.), thus allowing for production and, if desired, isolation of large amounts of a desired product. However, the ability to express, for example, functional mammalian polypeptides, including protein complexes, in the chloroplasts of any plant allows for production of crops of such plants and, therefore, the ability to conveniently produce large amounts of the polypeptides.

In one embodiment, a method of expressing a chimeric gene is disclosed including transforming an algae cell by replacing an endogenous chloroplast gene via integration of a chimeric construct having a heterologous coding sequence, a promoter sequence, and at least one UTR, wherein the promoter is cognate or non-cognate to the endogenous chloroplast gene, and cultivating the transformed algae cell. In one aspect, a gene product encoded by the heterologous coding sequence is constitutively expressed. In a related aspect, the cells are homoplasmic for the integration.

In one aspect, the heterologous coding sequence is driven by a non-cognate promoter of the replaced endogenous chloroplast gene. In another aspect, the chimeric construct comprises at least one non-cognate UTR to the endogenous chloroplast gene. Further, the endogenous gene includes, but is not limited to, a chloroplast gene encoding a photosystem-II (PSII) reaction center protein.

In another aspect, the replaced endogenous gene is re-inserted at a silent distal site, including that the endogenous gene may be re-inserted at a distal site is driven by a cognate or non-cognate promoter.

In one aspect, when the chimeric construct and the inserted distal endogenous gene are driven by the same cognate promoter, the gene product of the heterologous coding sequence is repressed. In another aspect, when the endogenous gene is driven by a non-cognate promoter, the gene product encoded by the heterologous coding sequence is not repressed.

In a related aspect, the expression of the gene product is modulated by light.

In another embodiment, a method of expressing a chimeric gene includes transforming an algae cell by replacing psbA via integration of a chimeric construct comprising a nucleic acid sequence encoding SEQ ID NO:2, a promoter sequence, and at least one UTR, where the promoter is cognate or non-cognate to the endogenous chloroplast gene, and cultivating the transformed algae cell. In one aspect, the at least one UTR is psbA or psbD UTRs. In a related aspect, the nucleic acid sequence (e.g., SEQ ID NO:1) is driven by a psbA or psbD promoter.

In another aspect, the psbA is re-inserted at a silent distal site. Further, the psbA at the distal site may be driven by a psbA or psbD promoter. In one aspect, the distal site is psbH.

In one embodiment, an algae cell transformed by the methods of the invention is disclosed, where the algae includes, but is not limited to, *Chlamydomonas reinhardtii*.

Accordingly, the methods of the invention can be practiced using any plant having chloroplasts, including, for example, macroalgae, for example, marine algae and seaweeds, as well as plants that grow in soil, for example, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea ultilane*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, duckweed (Lemna), barley, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals such as azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum are also included. Additional ornamentals useful for practicing a method of the invention include impatiens, Begonia, Pelargonium, Viola, Cyclamen, Verbena, Vinca, Tagetes, Primula, Saint Paulia, Agertum, Amaranthus, Antihirrhinum, Aquilegia, Cineraria, Clover, Cosmo, Cowpea, Dahlia, Datura, Delphinium, Gerbera, Gladiolus, Gloxinia, Hippeastrum, Mesembryanthemum, Salpiglossos, and Zinnia. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga ultilane*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Leguminous plants useful for practicing a method of the invention include beans and peas. Beans include guar, locust bean, fenugreek, soybean, garden beans, cowpea, mung bean, lima bean, fava bean, lentils, chickpea, etc. Legumes include, but are not limited to, *Arachis*, e.g., peanuts, *Vicia*, e.g., crown vetch, hairy vetch, adzuki bean, mung bean, and chickpea, *Lupinus*, e.g., lupine, trifolium, *Phaseolus*, e.g., common bean and lima bean, *Pisum*, e.g., field bean, *Melilotus*, e.g., clover, *Medicago*, e.g., alfalfa, *Lotus*, e.g., trefoil, *lens*, e.g., lentil, and false indigo. Preferred forage and turf grass for use in the methods of the invention include alfalfa, orchard grass, tall fescue, perennial ryegrass, creeping bent grass, and redtop. Other plants useful in the invention include *Acacia*, aneth, artichoke, arugula, blackberry, canola, cilantro, clementines, escarole, eucalyptus, fennel, grapefruit, honey dew, jicama, kiwifruit, lemon, lime, mushroom, nut, okra, orange, parsley, persimmon, plantain, pomegranate, poplar, radiata pine, radicchio, Southern pine, sweetgum, tangerine, triticale, vine, yams, apple, pear, quince, cherry, apricot, melon, hemp, buckwheat, grape, raspberry, chenopodium, blueberry, nectarine, peach, plum, strawberry, watermelon, eggplant, pepper, cauliflower, Brassica, e.g., broccoli, cabbage, ultilan sprouts, onion, carrot, leek, beet, broad bean, celery, radish, pumpkin, endive, gourd, garlic, snapbean, spinach, squash, turnip, ultilane, chicory, groundnut and zucchini.

A method of the invention can generate a plant containing chloroplasts that are genetically modified to contain a stably integrated polynucleotide (i.e., transplastomes; see, for example, Hager and Bock, Appl. Microbiol. Biotechnol. 54:302-310, 2000; see, also, Bock, supra, 2001). The integrated polynucleotide can comprise, for example, an encoding polynucleotide operatively linked to a first and second UTR as defined herein. Accordingly, the present invention further provides a transgenic (transplastomic) plant, which comprises one or more chloroplasts containing a polynucleotide encoding one or more heterologous polypeptides, including polypeptides that can specifically associate to form a functional protein complex.

The term "plant" is used broadly herein to refer to a eukaryotic organism containing plastids, particularly chloroplasts, and includes any such organism at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or a cultured cell, or can be part of higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like.

A method of producing a heterologous polypeptide or protein complex in a chloroplast or in a transgenic plant of the invention can further include a step of isolating an expressed polypeptide or protein complex from the plant cell chloroplasts. As used herein, the term "isolated" or "substantially purified" means that a polypeptide or polynucleotide being referred to is in a form that is relatively free of proteins, nucleic acids, lipids, carbohydrates or other materials with which it is naturally associated. Generally, an isolated polypeptide (or polynucleotide) constitutes at least twenty percent of a sample, and usually constitutes at least about fifty percent of a sample, particularly at least about eighty percent of a sample, and more particularly about ninety percent or ninety-five percent or more of a sample.

In one embodiment, an algae extract obtained from an algae cell transformed by replacing an endogenous chloroplast gene via integration of a chimeric construct having a heterologous coding sequence, a promoter sequence, and at least one UTR, where the promoter is cognate or non-cognate to the endogenous chloroplast gene is disclosed. In one aspect, the replaced gene is psbA and a product encoded by the heterologous coding sequence is a peptide as set forth in SEQ ID NO:2. In a related aspect, the peptide comprises approximately 0.25% to about 6% of the total protein in the extract. In another aspect, the algae is Chlamydomonas reinhardtii.

The term "heterologous" is used herein in a comparative sense to indicate that a nucleotide sequence (or polypeptide) being referred to is from a source other than a reference source, or is linked to a second nucleotide sequence (or polypeptide) with which it is not normally associated, or is modified such that it is in a form that is not normally associated with a reference material. For example, a polynucleotide encoding an antibody is heterologous with respect to a nucleotide sequence of a plant chloroplast, as are the components of a recombinant nucleic acid molecule comprising, for example, a first nucleotide sequence operatively linked to a second nucleotide sequence, and is a polynucleotide introduced into a chloroplast where the polynucleotide is not normally found in the chloroplast.

The chloroplasts of higher plants and algae likely originated by an endosymbiotic incorporation of a photosynthetic prokaryote into a eukaryotic host. During the integration process genes were transferred from the chloroplast to the host nucleus (Gray, Curr. Opin. Gen. Devel. 9:678-687, 1999). As such, proper photosynthetic function in the chloroplast requires both nuclear encoded proteins and plastid encoded proteins, as well as coordination of gene expression between the two genomes. Expression of nuclear and chloroplast encoded genes in plants is acutely coordinated in response to developmental and environmental factors.

In chloroplasts, regulation of gene expression generally occurs after transcription, and often during translation initiation. This regulation is dependent upon the chloroplast translational apparatus, as well as nuclear-encoded regulatory factors (see Barkan and Goldschmidt-Clermont, Biochemie 82:559-572, 2000; Zerges, Biochemie 82:583-601, 2000; Bruick and Mayfield, supra, 1999). The chloroplast translational apparatus generally resembles that in bacteria; chloroplasts contain 70S ribosomes; have mRNAs that lack 5' caps and generally do not contain 3' poly-adenylated tails (Harris et al., Microbiol. Rev. 58:700-754, 1994); and translation is inhibited in chloroplasts and in bacteria by selective agents such as chloramphenicol.

Several RNA elements that act as mediators of translational regulation have been identified within the 5'UTR's of chloroplast mRNAs (Alexander et al., Nucl. Acids Res. 26:2265-2272, 1998; Hirose and Sugiura, EMBO J. 15:1687-1695, 1996; Mayfield et al., J. Cell Biol. 127:1537-1545, 1994; Sakamoto et al., Plant J. 6:503-512, 1994; Zerges et al., supra, 1997). These elements may interact with nuclear-encoded factors and generally do not resemble known prokaryotic regulatory sequences (McCarthy and Brimacombe, Trends Genet. 10:402-407, 1994).

The term "regulatory element" is used broadly herein to refer to a nucleotide sequence that regulates the transcription or translation of a polynucleotide or the localization of a polypeptide to which it is operatively linked. An expression control sequence can be a promoter, enhancer, transcription terminator, an initiation (start) codon, a splicing signal for intron excision and maintenance of a correct reading frame, a STOP codon, an amber or ochre codon, an IRES, an RBS, or a sequence that targets a polypeptide to a particular location, for example, a cell compartmentalization signal, which can be useful for targeting a polypeptide to the cytosol, nucleus, plasma membrane, endoplasmic reticulum, mitochondrial membrane or matrix, chloroplast membrane or lumen, medial trans-Golgi cisternae, or a lysosome or endosome. Cell compartmentalization domains are well known in the art and include, for example, a peptide containing amino acid residues 1 to 81 of human type II membrane-anchored protein galactosyltransferase, or amino acid residues 1 to 12 of the presequence of subunit IV of cytochrome c oxidase (see, also, Hancock et al., EMBO J 10:4033-4039, 1991; Buss et al., Mol. Cell. Biol. 8:3960-3963, 1988; U.S. Pat. No. 5,776,689). Inclusion of a cell compartmentalization domain in a polypeptide produced using a method of the invention can allow use of the polypeptide, which can comprise a protein complex, where it is desired to target the polypeptide to a particular cellular compartment in a cell.

A vector or other recombinant nucleic acid molecule of the invention can include a nucleotide sequence encoding a reporter polypeptide or other selectable marker. The term "reporter" or selectable marker" refers to a polynucleotide (or encoded polypeptide) that confers a detectable phenotype. A reporter generally encodes a detectable polypeptide, for example, a green fluorescent protein or an enzyme such as luciferase, which, when contacted with an appropriate agent (a particular wavelength of light or luciferin, respectively) generates a signal that can be detected by eye or using appropriate instrumentation (Giacomin, Plant Sci. 116:59-72, 1996; Scikantha, J. Bacteriol. 178:121, 1996; Gerdes, FEBS Lett. 389:44-47, 1996; see, also, Jefferson, EMBO J. 6:3901-3907, 1997, fl-glucuronidase). A selectable marker generally is a molecule that, when present or expressed in a cell, provides a selective advantage (or disadvantage) to the cell containing the marker, for example, the ability to grow in the presence of an agent that otherwise would kill the cell.

A selectable marker can provide a means to obtain prokaryotic cells or plant cells or both that express the marker and, therefore, can be useful as a component of a vector of the invention (see, for example, Bock, supra, 2001). Examples of selectable markers include those that confer antimetabolite resistance, for example, dihydrofolate reductase, which confers resistance to methotrexate (Reiss, Plant Physiol. (Life Sci. Adv.) 13:143-149, 1994); neomycin phosphotransferase, which confers resistance to the aminoglycosides neomycin, kanamycin and paromycin (Herrera-Estrella, EMBO J. 2:987-995, 1983), hygro, which confers resistance to hygromycin (Marsh, Gene 32:481-485, 1984), trpB, which allows cells to utilize indole in place of tryptophan; hisD, which allows cells to utilize histinol in place of histidine (Hartman, Proc. Natl. Acad. Sci., USA 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: Current Communications in Molecular Biology, Cold Spring Harbor Laboratory ed.); and deaminase from Aspergillus terreus, which confers resistance to Blasticidin S (Tamura, Biosci. Biotechnol. Biochem. 59:2336-2338, 1995). Additional selectable markers include those that confer herbicide resistance, for example, phosphinothricin acetyltransferase gene, which confers resistance to phosphinothricin (White et al., Nucl. Acids Res. 18:1062, 1990; Spencer et al., Theor. Appl. Genet. 79:625-631, 1990), a mutant EPSPV-synthase, which confers glyphosate resistance (Hinchee et al., BioTechnology 91:915-922, 1998), a mutant acetolactate synthase, which confers imidazolione or sulfonylurea resistance (Lee et al., EMBO J. 7:1241-1248, 1988), a mutant psbA, which confers resistance to atrazine (Smeda et al., Plant Physiol. 103:911-917, 1993), or a mutant protoporphyrinogen oxidase (see U.S. Pat. No. 5,767,373), or other markers conferring resistance to an herbicide such as glufosinate. Selectable markers include polynucleotides that confer dihydrofolate reductase (DHFR) or neomycin resistance for eukaryotic cells and tetracycline; ampicillin resistance for prokaryotes such as E. coli; and bleomycin, gentamycin, glyphosate, hygromycin, kanamycin, methotrexate, phleomycin, phosphinotricin, spectinomycin, streptomycin, sulfonamide and sulfonylurea resistance in plants (see, for example, Maliga et al., Methods in Plant Molecular Biology, Cold Spring Harbor Laboratory Press, 1995, page 39). Since a composition or a method of the invention can result in expression of a polypeptide in chloroplasts, it can be useful if a polypeptide conferring a selective advantage to a plant cell is operatively linked to a nucleotide sequence encoding a cellular localization motif such that the polypeptide is translocated to the cytosol, nucleus, or other subcellular organelle where, for example, a toxic effect due to the selectable marker is manifest (see, for example, Von Heijne et al., Plant Mol. Biol. Rep. 9: 104, 1991; Clark et al., J. Biol. Chem. 264:17544, 1989; della Cioppa et al., Plant Physiol. 84:965, 1987; Romer et al., Biochem. Biophys. Res. Comm. 196:1414, 1993; Shah et al., Science 233:478, 1986; Archer et al., J. Bioenerg Biomemb. 22:789, 1990; Scandalios, Prog. Clin. Biol. Res. 344:515, 1990; Weisbeek et al., J. Cell Sci. Suppl. 11: 199, 1989; Bruce, Trends Cell Biol. 10:440, 2000.

The ability to passage a shuttle vector of the invention in a prokaryote allows for conveniently manipulating the vector. For example, a reaction mixture containing the vector and putative inserted polynucleotides of interest can be transformed into prokaryote host cells such as E. coli, amplified and collected using routine methods, and examined to identify vectors containing an insert or construct of interest. If desired, the vector can be further manipulated, for example, by performing site directed mutagenesis of the inserted polynucleotide, then again amplifying and selecting vectors having a mutated polynucleotide of interest. The shuttle vector then can be introduced into plant cell chloroplasts, wherein a polypeptide of interest can be expressed and, if desired, isolated according to a method of the invention.

A polynucleotide or recombinant nucleic acid molecule of the invention, which can be contained in a vector, including a vector of the invention, can be introduced into plant chloroplasts using any method known in the art. As used herein, the term "introducing" means transferring a polynucleotide into a cell, including a prokaryote or a plant cell, particularly a plant cell plastid. A polynucleotide can be introduced into a cell by a variety of methods, which are well known in the art and selected, in part, based on the particular host cell. For example, the polynucleotide can be introduced into a plant cell using a direct gene transfer method such as electroporation or microprojectile mediated (biolistic) transformation using a particle gun, or the "glass bead method" (see, for example, Kindle et al., supra, 1991), or by liposome-mediated transformation, transformation using wounded or enzyme-degraded immature embryos (see Potrykus, Ann. Rev. Plant. Physiol. Plant Mol. Biol. 42:205-225, 1991).

Plastid transformation is a routine and well known method for introducing a polynucleotide into a plant cell chloroplast (see U.S. Pat. Nos. 5,451,513, 5,545,817, and 5,545,818; WO 95/16783; McBride et al., Proc. Natl. Acad. Sci., USA 91:7301-7305, 1994). Chloroplast transformation involves introducing regions of chloroplast DNA flanking a desired nucleotide sequence into a suitable target tissue; using, for example, a biolistic or protoplast transformation method (e.g., calcium chloride or PEG mediated transformation). One to 1.5 kb flanking nucleotide sequences of chloroplast genomic DNA allow homologous recombination of the vector with the chloroplast genome, and allow the replacement or modification of specific regions of the plastome. Using this method, point mutations in the chloroplast 16S rRNA and rps12 genes, which confer resistance to spectinomycin and streptomycin, can be utilized as selectable markers for transformation (Svab et al., Proc. Natl. Acad. Sci., USA 87:8526-8530, 1990; Staub and Maliga, supra, 1992), and can result in stable homoplasmic transformants, at a frequency of approximately one per 100 bombardments of target tissues. The presence of cloning sites between these markers provides a convenient nucleotide sequence for making a chloroplast vector (Staub and Maliga, EMBO J. 12:601-606, 1993), including a vector of the invention. Substantial increases in transformation frequency are obtained by replacement of the recessive rRNA or r-protein antibiotic resistance genes with a dominant selectable marker, the bacterial a adA gene encoding the spectinomycin-detoxifying enzyme aminoglycoside-3'-adenyltransferase (Svab and Maliga, Proc. Natl. Acad. Sci., USA 90:913-917, 1993). Approximately 15 to 20 cell division cycles following transformation are-generally required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein.

A direct gene transfer method such as electroporation also can be used to introduce a polynucleotide of the invention into a plant protoplast (Fromm et al., Proc. Natl. Acad. Sci., USA 82:5824, 1985). Electrical impulses of high field strength reversibly permeabilize membranes allowing the introduction of the polynucleotide. Microinjection can be performed as described in Potrykus and Spangenberg (eds.), Gene Transfer To Plants (Springer Verlag, Berlin, N.Y. 1995). A transformed plant cell containing the introduced polynucleotide can be identified by detecting a phenotype due to the introduced polynucleotide, for example, expression of a reporter gene or a selectable marker.

Microprojectile mediated transformation also can be used to introduce a polynucleotide into a plant cell chloroplast (Klein et al., Nature 327:70-73, 1987). This method utilizes microprojectiles such as gold or tungsten, which are coated with the desired polynucleotide by precipitation with calcium chloride, spermidine or polyethylene glycol. The microprojectile particles are accelerated at high speed into a plant tissue using a device such as the BIOLISTIC PD-1000 particle gun (BioRad; Hercules Calif.). Methods for the transformation using biolistic methods are well known (Wan, Plant Physiol. 104:37-48, 1984; Vasil, BioTechnology 11: 1553-1558, 1993; Christou, Trends in Plant Science 1:423-431, 1996). Microprojectile mediated transformation has been used, for example, to generate a variety of transgenic plant species, including cotton, tobacco, corn, hybrid poplar and papaya. Important cereal crops such as wheat, oat, barley, sorghum and rice also have been transformed using microprojectile mediated delivery (Duan et al., Nature Biotech. 14:494-498, 1996; Shimamoto, Curr. Opin. Biotech. 5:158-162, 1994). The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, the glass bead agitation method (Kindle et al., supra, 1991), and the like.

Reporter genes have been successfully used in chloroplasts of higher plants, and high levels of recombinant protein expression have been reported. In addition, reporter genes have been used in the chloroplast of *C. reinhardtii*, but, in most cases very low amounts of protein were produced. Reporter genes greatly enhance the ability to monitor gene expression in a number of biological organisms. In chloroplasts of higher plants, .beta.-glucuronidase (uidA, Staub and Maliga, EMBO J. 12:601-606, 1993), neomycin phosphotransferase (nptII, Carrer et al., Mol. Gen. Genet. 241:49-56, 1993), adenosyl-3-adenyltransf-erase (aadA, Svab and Maliga, Proc. Natl. Acad. Sci., USA 90:913-917, 1993), and the *Aequorea victoria* GFP (Sidorov et al., Plant J. 19:209-216, 1999) have been used as reporter genes (Heifetz, Biochemie 82:655-666, 2000). Each of these genes has attributes that make them useful reporters of chloroplast gene expression, such as ease of analysis, sensitivity, or the ability to examine expression in situ.

Effective concentrations of the compounds provided herein or pharmaceutically acceptable salts or other derivatives thereof are mixed with a suitable pharmaceutical carrier or vehicle. Derivatives of the compounds, such as salts of the compounds or prodrugs of the compounds may also be used in formulating effective pharmaceutical compositions. The concentrations of the compounds are effective for delivery of an amount, upon administration, that ameliorates the symptoms of the disease. Typically, the compositions are formulated for single dosage administration.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

Pharmaceutical carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients.

The active compounds can be administered by any appropriate route, for example, orally, parenterally, intravenously, intradermally, subcutaneously, or topically, in liquid, semi-liquid or solid form and are formulated in a manner suitable for each route of administration. Preferred modes of administration include oral and parenteral modes of administration. The active compound is included in the pharmaceutically acceptable carrier in an amount sufficient to exert a therapeutically useful effect in the absence of undesirable side effects on the patient treated.

The therapeutically effective concentration may be determined empirically by testing the compounds in known in vitro and in vivo systems as described herein or known to those of skill in this art and then extrapolated therefrom for dosages for humans.

The concentration of active compound in the drug composition will depend on absorption, inactivation and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient. Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

In one embodiment, a method of treating intestinal bacterial or viral infection comprising administering to a subject in need thereof a therapeutically effective amount of an algae obtained from an algae cell transformed by replacing an endogenous chloroplast gene via integration of a chimeric construct having a heterologous coding sequence, a promoter sequence, and at least one UTR, wherein the promoter is cognate or non-cognate to the endogenous chloroplast gene. In a related aspect, the subject is a mammalian newborn or a mammalian infant. In a further related aspect, the mammalian subject is human, bovine, or porcine subject.

In one aspect, wherein the algae comprises a peptide as set forth in SEQ ID NO:2. In a related aspect, the bacterial infection comprises exposure to an enteropathogenic *Escherichia coli*. In another related aspect, the bacterial infection is necrotizing enterocolitis or infectious diarrhea.

In one embodiment, the protein expressed in the algae is delivered by oral administration in the form of an extract. In one aspect, the algae is administered prophylactically. As used herein, "prophylactic," including grammatical variations thereof, means guarding from or preventing disease.

The tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors. The active materials can also be mixed with other active materials which do not impair the desired action, or with materials that supplement the desired action.

In addition, the algae-based production platform as disclosed provides for certain therapeutic approaches, such as oral delivery of a vaccine, antibody or cytokine, especially when the principle target tissue is the gut. High level accumulation of recombinant proteins in an edible form, with the alga cell wall conferring protection from the acidic gastric environment, is also disclosed.

EXAMPLES

Using a variety of endogenous promoters and 5' untranslated regions vectors were identified that allow for expression of recombinant proteins, up to 1% of total soluble protein, and all of these proteins accumulate in the soluble phase of the plastid and appear to be correctly folded. Using a luciferase reporter gene expression of the reporter was highest when the chimeric gene was transformed into a recipient strain that lacked the corresponding endogenous gene, suggesting that expression of the chimeric mRNA might be improved when the endogenous mRNA was lacking. To directly test this hypothesis two vectors were generated for the expression of a mammalian protein, bovine mammary associated serum amyloid A3 (M-SAA3). M-SAA3 was chosen because the protein is found in the colostrums of mammals and has been shown to induce mucin synthesis in gut epithelial cells, potentially resulting in protection against intestinal bacterial and viral infections in newborns (Larson et al 2002). The production of M-SAA3 in algae could potentially provide this protective agent for mammals that lack a source of colostrums. The first vector examined was based on the psbD promoter and UTR, which was observed to be the best promoter/UTR combination for driving expression of a GFP reporter. The second vector examined contained the psbA promoter and UTR, and was designed to replace the endogenous psbA gene upon integration of the chimeric gene into the chloroplast genome. Such replacement of the endogenouspsbA gene with a chimeric psbA-SAA gene results in expression of M-SAA3 to greater than 5% of total soluble protein, levels that make economic production of this protein possible. Also algal expressed M-SAA is able to stimulate mucin production in a human gut epithelial cell line. These data demonstrate the utility of micro-algae as a production platform for human therapeutic proteins, and also suggest that bioactive proteins can function in a crude non-purified mix of algal proteins, demonstrating the potential of using this algae as a delivery vehicle for gut active therapeutic proteins.

Example 1

Materials and Methods

*C. reinhardtii* Strains, Transformation and Growth Conditions.

Transformations were carried out on *C. reinhardtii* wild type strain 137c (Franklin et al., Plant J. 30 (2002) 30:733-744). Cells were grown to late log phase (approximately seven days) in the presence of 40 mM 5-Fluorodeoxyuridine in TAP medium (Gorman and Levine, Proc Natl Acad Sci USA (1965) 54:1665-1669) at 23° C. under constant illumination of 4,000 lux (high light) on a rotary shaker set at 100 rpm. 50 ml of cells were harvested by centrifugation at 4,000×g at 4° for 5 min. The supernatant was decanted and cells resuspended in 4 ml TAP medium for subsequent chloroplast transformation by particle bombardment as described previously in Cohen et al. (Meth Enzymol (1998) 297:192-208). All transformations were carried out under spectinomycin selection (150 µg/ml) in which resistance was conferred by co-transformation with the spectinomycin resistance ribosomal gene of plasmid p228 (Chlamydomonas Stock Center, Duke University).

Cultivation of *C. reinhardtii* transformants for expression of M-SAA3 was carried out in TAP medium (Gorman and Levine, 1965, supra) at 23° C. under constant illumination.

Plasmid Construction.

All DNA and RNA manipulations were carried out essentially as described in Sambrook et al. (1989, supra) and Cohen et al. (1998, supra). The coding region of the M-SAA3 gene was synthesized de novo according to the method of Stemmer et al. (Gene (1995) 164:49-53) from a pool of primers, each 40 nucleotides in length. The 5' and 3' terminal primers used in this assembly contained restriction sites for Nde I and Xba I, respectively. The resulting PCR product containing was cloned into plasmid pCR2.1 TOPO (Invitrogen, Inc.) according to the manufacturers protocol to generate plasmid pM- SAA3. The psbD (D2) and psbA promoters and 5' UTR and the psbA 3' UTR were generated as described in Barnes et al., (Mol Genet Genomics (2005) 274(6):625-636). Chloroplast transformation plasmid p322 was constructed as described in Franklin et al. (2002, supra).

Southern and Northern Blots.

Southern blots and $^{32}$P labeling of DNA for use as probes were carried out as described in Sambrook et al. (1989, supra), and Cohen et al. (1998, supra). Radioactive probes used on Southern blots included the Nde I/Xba I M-SAA3 coding region of M-SAA3 (probe M-SAA3), and a 2.0 kb BamH I/Xho I fragment of p322 (probe 3' p322). A 0.5 kb Nde-Pst fragment from the coding region of the psbA gene was used as the psbA specific probe. Additional radioactive probes used in Northern blot analysis included the rbcL cDNA as a control on Northern blots. Northern and Southern blots were visualized utilizing a Pakard Cyclone Storage Phosphor System equipped with Optiquant software.

Protein Expression and Western Blotting and Luciferase Assays.

Plasmidsp-SAACt was transformed into *E. coli* strain BL21 and cells grown overnight in liquid media. For Western blot analysis proteins were isolated from *E. coli* or from *C. reinhardtii* utilizing a buffer containing 750 mM Tris·Cl, pH 8.0, 15% sucrose (wt/vol), 100 mM β mercaptoethanol, 1 mM phenylmethylsulfonylfluoride (PMSF). Samples were then centrifuged for 30 min at 13,000×g at 4° C. with the resulting supernatant used in Western blot analysis. Western blots were carried out as described in Cohen et al. (1998, supra) using a rat anti-SAA monoclonal primary antibody (gift of A. Weber and T. McDonald) and an alkaline phosphatase labeled goat anti-rabbit secondary antibody (Sigma).

Mucin 3(MUC3) Induction Assays.

Human HT29 cells were used for MUC3 induction assay. Cells were grown in 5% $CO_2$ at 37° C. after adaptation in glucose-free McCoys 5A medium containing 5 mM galactose and antibiotics. Cells were grown to sub-confluency in 48 well tissue culture plates prior to performing mucin induction assays. Peptides used for induction assays correspond to the first 10 amino acids of human M-SAA (RWGTFLKEAG (SEQ ID NO:10)), or a scrambled version of the same sequence (GKFAWEGMTL (SEQ ID NO:11)). In order to release the active peptide, and to mimic the proteolytic environment of the gut, purified algal M-SAA was partially digested with clostripain, endo arginine C, or trypsin prior to use in induction assay. Peptides (50 µg/mL) or purified digested algal M-SAA (approx. 150 µg/mL) were added to cell cultures either one or every hour for four hours, after which cell culture media was collected and blotted to nitrocellulose membrane using slot blotting apparatus. MUC3 monoclonal and alkaline phosphatase-conjugated goat anti-mouse antibodies were hybridized to the slot blots, which were subsequently developed. Quantitation of slot blots was accomplished using IMAGEJ™ software (NIH).

Example 2

De novo Synthesis of a Bovine Mammary Associated Serum Amyloid A3 Gene in *C. reinhardtii* Chloroplast Codon Bias In order to obtain high levels of protein expression in algal chloroplast synthesis of coding region in codons optimized to reflect abundantly expressed genes of the *C. reinhardtii* chloroplast (Franklin et al., 2002, supra; Mayfield and Schultz, Plant J (2004) 37:449-458) was required. The chloroplast mammary associated serum amyloid A3 gene (M-SAA3, FIG. 1) was designed based on the M-SAA3 gene from bovine (McDonald et al., Vet Immunol Immunopathol (1999) 83:203-211). The M-SAA3 sequence was obtained from Genbank (AF335552), and a series of oligos were designed based upon this amino acid sequence, but changing codon usage to reflect those of highly expressed *C. reinhardtii* chloroplast genes. The gene was assembled using PCR by the method of Stemmer et al. (1995, supra). PCR products were cloned into *E. coli* plasmids, the synthetic gene sequenced, and errors corrected by site directed mutagenesis. An NdeI site was placed at the initiation codon and an Xba I site placed immediately downstream of the stop codon, for ease in subsequent cloning.

Example 3

Construction of an M-SAA3 Expression Cassette and Southern Blot Analysis of M-SAA3 Transformants Once it was determined that the M-SAA3 coding sequence was correct, chloroplast M-SAA3 expression cassettes were constructed. An expression cassette containing the psbD promoter and 5' UTR, and the psbA 3' UTR was constructed initially. This construct was made because the psbD 5' UTR gave the best expression, of five promoters examined, of a recombinant green fluorescent protein in transgenic chloroplast (Barnes et al., 2005, supra). The M-SAA3 coding sequence was ligated down stream of the psbD promoter and 5' UTR, and upstream of the psbA 3' UTR (FIG. 2). The chimeric psbD/M-SAA3 gene was then ligated into chloroplast transformation plasmid p322 (Franklin et al., 2002, supra) at the unique Bam HI site to create plasmid p322-psbD/M-SAA3 and transformed into wt *C. reinhardtii*.

Figure 3:
FIG. 3 shows: Southern blot analysis of psbD-M-SAA3 chloroplast transformants. *C. reinhardtii* DNAs were prepared as described in experimental procedures, digested with BamHI or with EcoR I and Xho I and subjected to Southern blot analysis. Filters were hybridized with the radioactive probes indicated in the figure.

Wild type *C. reinhardtii* cells (137c) were transformed with the p322-psbD/M-SAA3 plasmid and the selectable marker plasmid p228, conferring resistance to spectinomycin. Primary transformants were screened for the presence of the M-SAA3 gene by Southern blot analysis, and positive transformants were taken through additional rounds of selection to isolate homoplasmic lines in which all copies of the chloroplast genome contained the introduced M-SAA3 gene. Two homoplasmic M-SAA3 transformants, D2-SAA1 and D2-SAA7, were selected for further analysis. Correct integration of the plasmid p322-psbD/M-SAA3 into the chloroplast genome was ascertained using either the Nde I-Xba I fragment of M-SAA3, or the Bam HI-Xho I fragment of plasmid p322 as probes. Genomic DNA from wt and the two M-SAA3 transformants was digested with Bam HI or with EcoR I and Xho I, fractionated on agarose gels, and subjected to Southern blot analysis. As shown in FIG. 3, the two transformants contained M-SAA3 hybridizing bands, while the wild type strain had no signal with this M-SAA3 coding region probe. Hybridization with the Bam HI - Xho I fragment from the p322 plasmid (FIG. 3) identifies a single band in wt and a different band in the two transformants, and each of these bands is of the correct predicted size for both the wt and transformant lines. These data demonstrate that the D2-SAA gene had correctly integrated into the chloroplast genome and that the two transgenic lines are homoplasmic.

Example 4

Analysis of M-SAA3 Protein Accumulation in Transgenic C. reinhardtii Chloroplasts To determine if M-SAA3 protein accumulated in the psbD-SAA transgenic lines, M-SAA3 was measured by Western blot analysis. Twenty μg of total soluble protein (tsp) from wt and the two transgenic lines was separated by SDS-PAGE and either stained with Coomassie, or subjected to Western blot analysis. The Coomassie stained gel (FIG. 4, left panel) indicates that equal amounts of protein were loaded in each lane, and that the transgenic lines accumulate a similar set of proteins as compared to wt. Western blot analysis of the same samples identified a single band corresponding to the SAA protein in both of the psbD-M-SAA3 transgenic lanes (FIG. 4, right panel). No signal was observed in the wt C. reinhardtii lane, as expected. The amount of SAA protein in the two transgenic lines was similar and was quantitated by comparison with a serial dilution a purified recombinant M-SAA3 protein. SAA accumulated to approximately 0.5% of total soluble protein in each strain.

Example 5

Construction of a psbA Gene Replacement Containing the M-SAA3 Gene

Expression of a recombinant luciferase gene was observed to be higher in a mutant lacking the psbA gene compared to expression of the same gene in a wt strain (Mayfield and Schultz, 2004, supra). To identify if recombinant proteins were generally expressed at higher levels in psbA deletion strains, or if this was restricted to recombinant protein expression in this specific psbA mutant, a transformation cassette was generated that would result in the deletion (replacement) of the psbA gene upon integration of the psbA-M-SAA3 gene. As shown in FIG. 5 the M-SAA3 coding region was ligated down stream of a 1.5 kb fragment of the chloroplast genome that contains the psbA promoter and 5' UTR. The 3' UTR of psbA was ligated downstream of the M-SAA coding region. A second recombinant gene containing the rbcL promoter and 5' UTR followed by the luxCt coding region and then the rbcL 3' UTR, was ligated downstream of the psbA-M-SAA gene. This second reporter gene was placed in the cassette so that expression of a recombinant protein from a promoter other than the psbA promoter in the psbA knockout strain could be monitored. A chloroplast genomic fragment corresponding to sequences downstream of the psbA gene was placed after the two recombinant genes to produce a construct, psbA/SAA/lux that should result in the integration of the M-SAA3 and luxCt genes in place of the psbA coding region.

Figure 6:
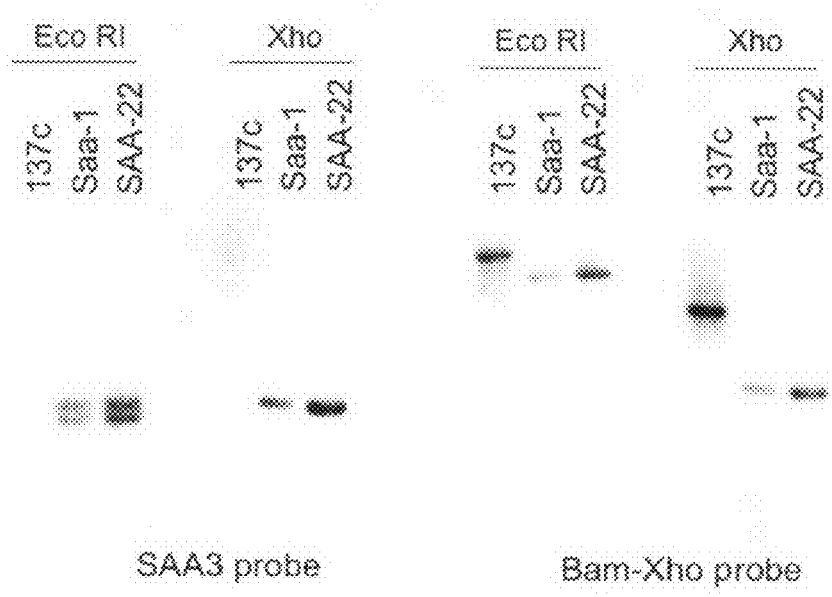
FIG. 6 shows Southern blot analysis of psbA-M-SAA chloroplast transformants. *C. reinhardtii* DNAs were prepared as described in experimental procedures, digested with EcoR I or Xho I and subjected to Southern blot analysis. Filters were hybridized with the radioactive probes indicated in the figure.

The psbA/SAA/lux plasmid was transformed into wt cells along with plasmid p228 and plated on spectinomycin. Transformants were selected and scored for SAA integration, and positive transformants were taken through additional rounds of selection to identify homoplasmic lines. Two homoplasmic lines psbA-SAA-1 and psbA-SAA-22 were identified and characterized in further detail. Correct integration of the plasmid psbA/SAA/lux into the chloroplast genome was ascertained using either the coding region of M-SAA3, the coding region of psbA, or the Bam HI-Xho I fragment of plasmid p322. Genomic DNA from wt and the two psbA-M-SAA3 transformants was digested with EcoR I or with Xho I, fractionated on agarose gels, and subjected to Southern blot analysis. As shown in FIG. 6, the two transformants contain M-SAA3 hybridizing bands, while the wild type strain has no signal with this M-SAA3 coding region probe. Hybridization with a psbA coding region probe showed that wt still contained the psbA coding region, while both of the SAA transformants lack the psbA coding sequence. Hybridization with the Bam-Xho probes of plasmid p322 produced a single band in all lanes, and each of these bands is of the correct predicted size for both the wt and transformant lines. These data demonstrate that the two transgenic lines are homoplasmic, and that the psbA coding region has been deleted upon integration of the psbA-M-SAA3 gene.

Example 6

Accumulation of M-SAA3 mRNA in Transgenic Strains

Figure 7:
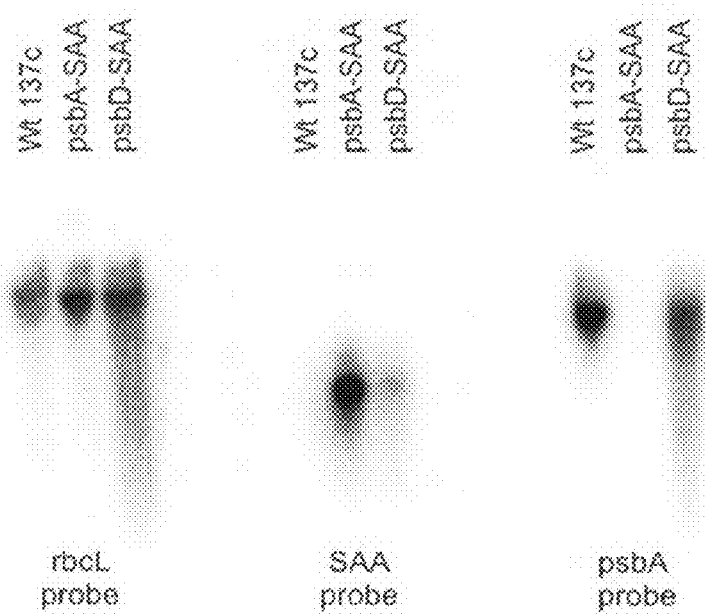
FIG. 7 shows detection of chloroplast expressed M-SAA3 mRNA in transgenic M-SAA *C. reinhardtii* strains. Total RNA isolated from untransformed (wt), psbA-M-SAA, and psbD-M-SAA transform ants was separated on denaturing agars gels and blotted to nylon membrane. The membranes were hybridized with a M-SAA3 coding region probe, an rbcL cDNA probe, or a psbA cDNA probe, as indicated under the panel.

To determine if the M-SAA3 gene was transcribed in transgenic C. reinhardtii chloroplasts, Northern blot analysis of total RNA was used. Ten pg of total RNA, isolated from wt, from psbD-SAA7, and psbA-SAA22 transgenic lines, was separated on denaturing agarose gels and blotted to nylon membrane. Duplicate filters were hybridized with a $^{32}$P labeled rbcL probe (FIG. 7, left panel), a M-SAA3 probe (FIG. 7, central panel), or a psbA coding region probe (FIG. 7, right panel). Each of the strains accumulate rbcL mRNA to similar levels, demonstrating that equal amounts of RNA were loaded for each lane, and that chloroplast transcription and mRNA accumulation are normal in the transgenic lines. Hybridization of the filters with the M-SAA3 specific probe (FIG. 7, central panel), showed that both transgenic lines accumulate M-SAA3 mRNA of the predicted size, while no M-SAA3 signal is observed in wt cells, as expected. The psbA-SAA strain accumulates significantly more M-SAA mRNA than the psbD-SAA strain.

Example 7

M-SAA3 Accumulates to Very High Levels in the psbA Knockout Strain

To determine M-SAA3 protein accumulation in the psbA knockout transgenic lines, M-SAA3 was measured by Western blot analysis. Twenty μg of total soluble protein (tsp) from wt and the two transgenic lines was separated by SDS-PAGE and either stained with Coomassie, or subjected to Western blot analysis. The Coomassie stained gel (FIG. 8, left panel) indicates that equal amounts of protein were loaded in each lane, and that the transgenic lines accumulate a similar set of proteins as compared to wt, with a notable exception of a prominent band of 12 kDa found in the transgenic lanes. Western blot analysis of the same samples identified the prominent 12 kDa band as corresponding to the M-SAA3 protein (FIG. 8, right panel). The amount of M-SAA protein in the two psbA-SAA transgenic lines was similar and was quantitated, by comparison with a serial dilution a purified recombinant M-SAA3 protein (FIG. 8 right panel), to equal 5% of total protein. Of this protein approximately two thirds was found in the soluble fraction and one third was found in the membrane fraction (compare lanes 5 and 7 of FIG. 8 left panel).

Example 8

Replacement of the psbA Gene at a Distal Site in the psbA-M-SAA Transgenic Line Results in Loss of M-SAA Expression To identify if the increased expression of the M-SAA in the psbA replacement strain was due to absence of the endogenous psbA gene and mRNA, or if it was to a position effect of the precise replace construct, the wt psbA gene at a distal site in the psbA-M-SAA transgenic line was re-introduced. To accomplish this, a psbA gene containing the psbA promoter and 5' UTR, the D1 coding region and psbA 3' UTR was ligated as a Bam HI fragment into the Bam HI site of plasmid p3HB. As shown in FIG. 9 A ligation of the psbA gene into this site allows for integration into the chloroplast genome at a silent site near the psbH gene, located at a distal site from the psbA-M-SAA integrated gene. Transgenic line M-SAA22 was transformed with the psbA-p3HB construct and selected on minimal media for photosynthetic growth, which should only occur if the psbA gene integrates and expresses D1 protein. Photosynthetic strains were examined for both psbA coding region and for the presence of the SAA gene. All transformants identified contained both genes.

Western blot analysis of the dually transformed lines showed that M-SAA failed to accumulate when D1 was re-expressed from a wt psbA gene reintroduced at the distal site (FIG. 10), showing that competition between the endogenous psbA gene and the chimeric psbA-M-SAA must account for the low level expression of the chimeric gene, and not any position affects of the precise replacement of the chimeric gene into the psbA locus.

Example 9

Replacement of the psbA Coding Region at a Distal Site with a Chimeric Gene Containing the psbD Promoter and UTR Allows for Photosynthetic Growth and Retains M-SAA Expression To identify if the absence of M-SAA accumulation in the presence of the psbA gene was due to competition from the promoter or UTR limiting protein expression, or was perhaps due to feedback from the D1 protein limiting expression from the chimeric psbA mRNA, as has been reported for several *C. reinhardtii* chloroplast mRNAs (Chochet et al., 2002, 2006), psbA-M-SAA expression in a strain that contained the wt D1 coding region driven by the psbD promoter and UTR was examined.

To accomplish this a chimeric psbA gene was constructed containing the psbD promoter and 5' UTR, the D1 coding region and psbA 3' UTR as a Bam HI fragment into the Bam HI site of plasmid p3HB. As shown in FIG. 9 B ligation of this chimeric psbA gene into this site allows for integration into the chloroplast genome at a silent site near the psbH gene, located at a distal site from the psbA-M-SAA integrated gene. Transgenic line M-SAA22 was transformed with the psbD-psbA-p3HB construct and selected on minimal media for photosynthetic growth, which should only occur if the psbD-psbA gene integrates and expresses D1 protein. Photosynthetic strains were examined for both psbA coding region and for the presence of the SAA gene, and confirmed to contain both genes.

Figure 10:
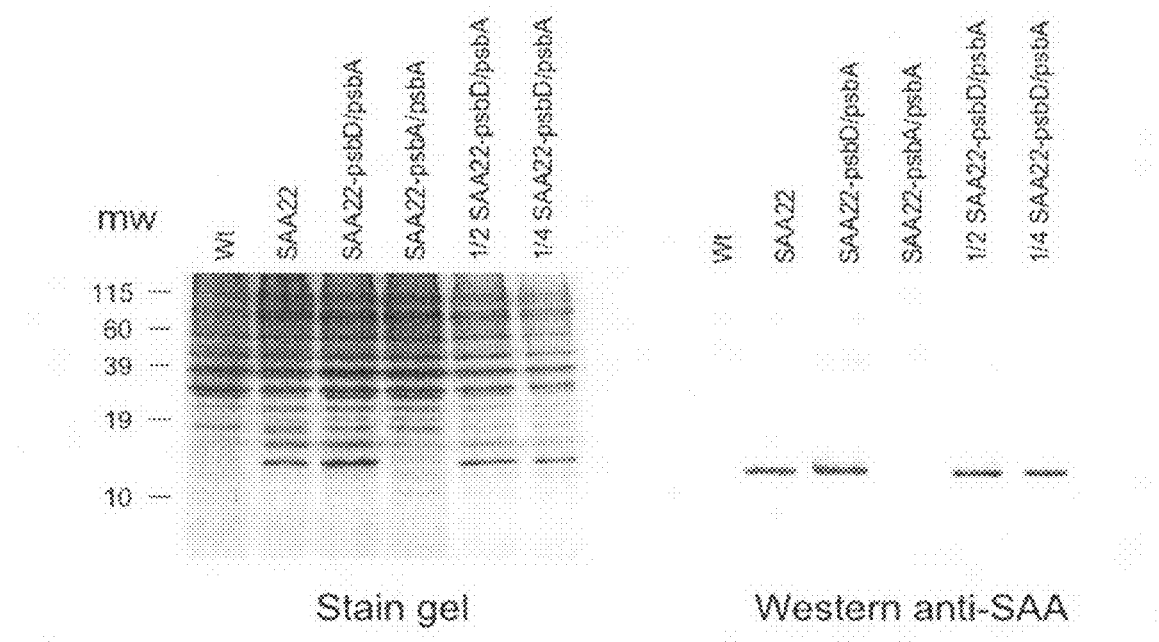
FIG. 10 shows the detection of chloroplast expressed M-SAA3 proteins in transgenic psbA-M-SAA *C. reinhardtii* strains with the psbA protein expressed at a distal site in the chloroplast genome. Ten 10 µg of total protein, from wt, starting strain psbA-M-SAA3 transgenic lines 22 (SAA22), SAA-22 transformed with a psbD-psbA chimeric gene, or apsbA-psbA wt gene, both at distal sites, was separated on 18% SDS PAGE and either stained with Coomassie blue (left panel) or transferred to nitrocellulose membranes and hybridized with anti-SAA antisera (right panel). Strains were grown in complete darkness for five days and then transferred to light for 24 hours before harvest. A one half and one quarter dilution of SAA22-psbD-psbA is run in the right two lanes for comparison.

Total proteins from wt. *C. reinhardtii*, the original psbA-M-SAA replacement strain, and the reintroduced psbA strains were assayed for D1 (psbA gene product) and M-SAA protein accumulation using western blot analysis. (FIG. 10).

M-SAA accumulation in the dually transformed and photosynthetic strain containing the chimeric construct showed nearly twice the accumulation of the parent psbA-M-SAA replacement strain. ELISA assays were also used to quantitate the level of M-SAA accumulation in this strain, and by this assay M-SAA was found to accumulate to 12.5% of total protein. As ELISA measures total protein, including breakdown products of M-SAA and aggregates of the protein which would not be detected in the western blot assay, ELISA values tend to be higher.

Example 10

Analysis of Algal Expressed M-SAA Protein

Algal expressed M-SAA was purified by reverse-phase chromatography using octyl-sepharose resin. M-SAA is a 112 amino acid protein with a predicted molecular mass of 12,673 mass units. Purified protein from fungal chloroplasts has a mass average of 12,690 mass units and appears predominantly as a single peak in MALDI analysis. This experimentally derived mass is within 0.1% of the predicted mass of the protein, within the error of the mass spectrometer, which is in good agreement with the size of algal expressed M-SAA on denaturing SDS-PAGE (FIGS. 8 and 10).

The predicted amino acid sequence of amine end of bovine M-SAA is MWGTFLKEAG (SEQ ID NO:12), and this exact sequence was identified in the purified protein. Chloroplasts, like bacteria, sometime remove the terminal methionine from a protein if the following amino acid is small. (Yamaguchi et al., J Biol Chem (2003) 278(36):33774-337785). With tryptophan as the second amino acid the initiation methionine was predicted to remain on the M-SAA protein, and the terminal methionine was clearly identified in the Edmund degradation analysis. These data confirm that chloroplast-expressed M-SAA is not modified to any significant degree.

Example 11

Accumulation of M-SAA3 mRNA in Transgenic Strains

Figure 11:
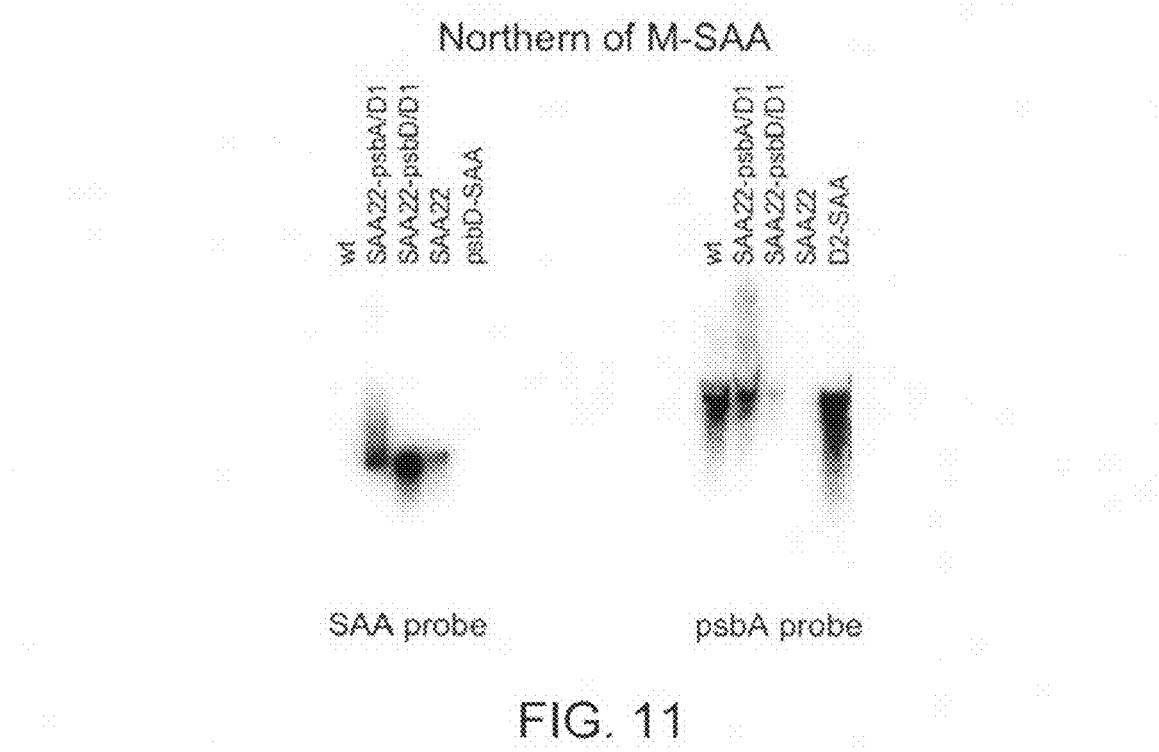
FIG. 11 illustrates the results of an Northern blot analysis of total RNA from wt, SAA22 transformed with psbA/psbA (D1), SAA22 transformed with psbD/psbA (D1), SAA22, and psbD-M-SAA. Filters were probed with either an SAA probe (left panel) or psbA probe (right panel).

The robust accumulation of M-SAA in the psbA knockout strains and the even higher accumulation in the psbD/psbA reintroduced strain led to the examination of M-SAA3 mRNA accumulation in transgenic *C. reinhardtii* chloroplasts. Northern blot analysis of ten μg of total RNA, isolated from wt, psbA-SAA22, and from the psbA/psbA and the psbD/psbA reintroduction transgenic lines, was separated on denaturing agarose gels and blotted to nylon membrane. Duplicate filters were hybridized with a $^{32}$P labeled M-SAA3 probe (FIG. 11, right panel), or psbA coding region probe (FIG. 11, left panel). Hybridization of the filters with the M-SAA3 specific probe showed that the original psbA-M-SAA transgenic line accumulate M-SAA mRNA of the predicted size, while no psbA signal was observed in this line as expected. The psbD/psbA M-SAA strain accumulates significantly more M-SAA mRNA than either the original M-SAA strain, or psbA/psbA M-SAA strain, which had similar amounts of M-SAA mRNA as the original strain. For psbA mRNA accumulation, the original psbA/M-SAA strain had no psbA mRNA as expected, while the psbA/psbA and psbD/

Example 12

Algal Expressed SAA Stimulates Mucin Production in Human Epithelial Cell Lines psbA both had psbA mRNA but less than wt, with the psbD/psbA having only one fifth of the psbA mRNA compared to wt.

Human intestinal epithelial cells, line HT29, were grown in 96 well microtiter plates at 37° C. in the presence of 5% $CO_2$. The cells were treated with either a synthetic peptide corresponding to the first ten amino acids of mature bovine SAA (in random order), or with algal expressed SAA treated with or without endo Arginine C, trypsin, or clostripain. Clostripain treatment partially digests the protein and releases a peptide containing the first 18 amino acids of the protein, a peptide similar to the human peptide positive control. Cells were treated with increasing amounts of peptide or digested protein over a period of 1 to 4 hours. Incubating HT29 cells with increasing amounts of the 10 amino acid SAA peptide, resulted in the induction of mucin 3 (MUC3) protein accumulation in the cells, as previously described (Larson et al., Biochem Biophys Res Commun (2003) 300:531-540). Treating the cells with increasing amount of purified algal expressed SAA, digested with either endo Arginine C, trypsin or clostripain, resulted in a similar increase in mucin production (approximately three fold, compared to controls).

Example 13

Increased Expression of Luciferase using the psbA Replacement

Figure 12:
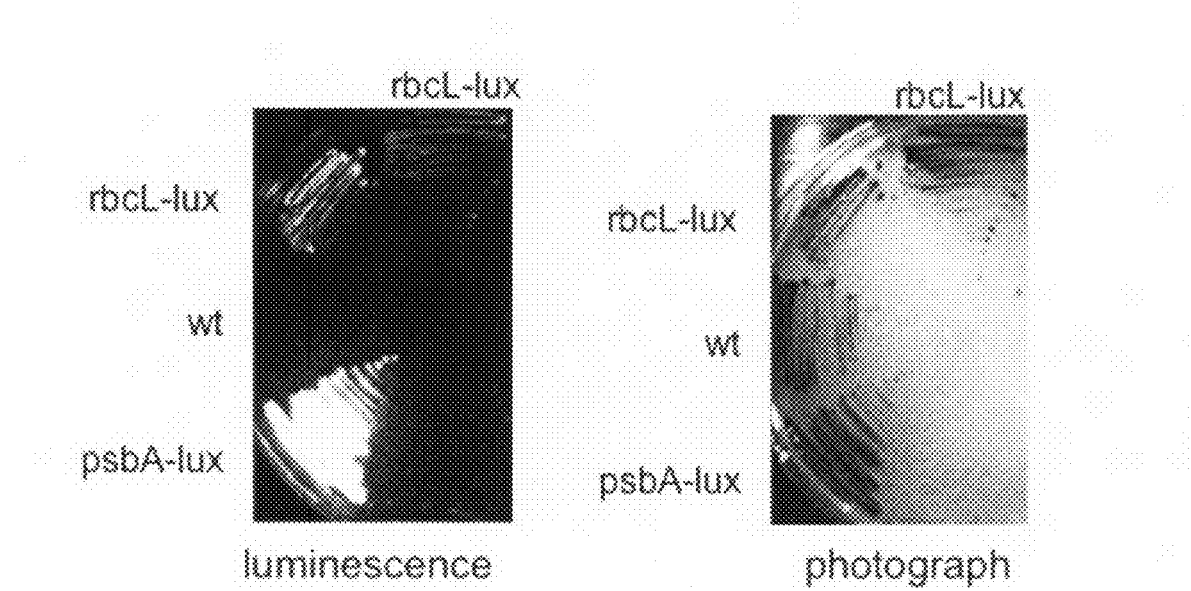
FIG. 12 shows the increased expression of luciferase driven by psbA promoter and 5' UTR as a replacement of the psbA gene (psbA-lux). A wild type strain (wt) and two different transgenic line with lux driven by the rbcL promoter and UTR (rbcL-lux) are shown for comparison.

To develop a sensitive reporter of gene expression in chloroplast, a luciferase gene was synthesized using codons optimized to reflect abundantly expressed genes of the *C. reinhardtii* chloroplast. The luciferase gene, lux, was driven by psbA and promoter and 5' UTR as a replacement of the psbA gene (psbA-lux). A wild type strain (wt) and two different transgenic line with lux driven by the rbcL promoter and UTR (rbcL-lux) are shown for comparison (FIG. 12). Luciferase activity, and hence luciferase protein expression, is much greater in the psbA replacement strain compared to expression of luciferase driven by rbcL placed in a silent site of the chloroplast genome. This data clearly shows that chimeric genes introduced as a replacement of an endogenous chloroplast gene has the potential for very high levels of recombinant protein expression.

Although the invention has been described with reference to the above examples, it will be understood that modifications and variations are encompassed within the spirit and scope of the invention. Accordingly, the invention is limited only by the following claims.

What is claimed is:

1. A method of expressing a gene comprising:
   transforming an algal cell by replacing an endogenous chloroplast gene via integration of a chimeric construct having a heterologous coding sequence, a promoter sequence cognate or non-cognate to the endogenous chloroplast gene, and at least one UTR, wherein the endogenous chloroplast gene is re-inserted at a silent distal site; and
   cultivating the transformed algal cell under conditions to allow for expression of the chimeric construct.

2. The method of claim 1, wherein the heterologous coding sequence is driven by a cognate promoter of the endogenous chloroplast gene.

3. The method of claim 1, wherein the chimeric construct comprises at least one non-cognate UTR to the endogenous chloroplast gene.

4. The method of claim 1, wherein the endogenous chloroplast gene exhibits autoregulation of translation.

5. The method of claim 4, wherein the endogenous chloroplast gene encodes a photosystem II (PSII) reaction center protein.

6. The method of claim 2, wherein the endogenous chloroplast gene re-inserted at the distal site is driven by a non-cognate promoter.

7. The method of claim 2, wherein the endogenous chloroplast gene re-inserted at the distal site is driven by a cognate promoter.

8. The method of claim 7, wherein a gene product of the heterologous coding sequence is repressed.

9. The method of claim 6, wherein expression of a gene product encoded by the heterologous coding sequence is not repressed.

10. The method of claim 9, wherein the expression of the gene product is modulated by light.

11. The method of claim 1, wherein a gene product encoded by the heterologous coding sequence is constitutively expressed.

12. The method of claim 5, wherein the transformed cell is cultivated in media for photosynthetic growth.

13. The method of claim 1, wherein the cells are homoplasmic for the integration.

14. The method of claim 1, wherein codons of the heterologous coding sequence are optimized to reflect abundantly expressed genes of the algal cell.

15. The method of claim 1, wherein the endogenous chloroplast gene is psbA.

16. The method of claim 2, wherein the cognate promoter is a psbA promoter.

17. The method of claim 6, wherein the non-cognate promoter is a psbD promoter.

18. The method of claim 1, wherein the heterologous coding sequence comprises SEQ ID NO:1.

19. The method of claim 1, wherein one UTR is a psbD 5' UTR.

20. The method of claim 1, wherein expression of the chimeric construct is determined by accumulation of mRNA encoded by the heterologous coding sequence.

21. The method of claim 1, wherein expression of the chimeric construct is determined by accumulation of protein encoded by the heterologous coding sequence.

22. The method of claim 1, wherein the heterologous coding sequence encodes a peptide, a protein, a protein complex, or a combination thereof.

23. The method of claim 22, wherein the heterologous coding sequence encodes a protein.

24. The method of claim 23, wherein the protein is a mammalian protein.

25. The method of claim 24, wherein the mammalian protein is bioactive in the gut.

26. The method of claim 23, wherein the protein is mammary associated serum amyloid A3 (M-SAA3).

27. The method of claim 26, wherein the M-SAA3 is bovine M-SAA3.

28. The method of claim 1, wherein the heterologous coding sequence is optimized for plastid codon usage.

29. The method of claim 23, wherein the protein is a reporter protein or a mutant variant thereof.

30. The method of claim 23, wherein the protein is a gut active protein.

31. An algal cell transformed by the method of claim 1.

32. The algal cell of claim 31, wherein the alga is *Chlamydomonas reinhardtii*.

33. A method of expressing a gene comprising:
transforming an algal cell by replacing psbA via integration of a chimeric construct comprising a nucleic acid sequence encoding SEQ ID NO:1, a promoter sequence cognate or non-cognate to psbA, and at least one UTR, wherein psbA is re-inserted at a silent distal site; and
cultivating the transformed algal cell under conditions to allow for expression of the chimeric construct.

34. The method of claim 33, wherein the at least one UTR is psbA or psbD UTRs.

35. The method of claim 33, wherein SEQ ID NO:1 is driven by a psbA or psbD promoter.

36. The method of claim 33, wherein psbA at the distal site is driven by a psbA or psbD promoter.

37. The method of claim 33, wherein the promoters driving SEQ ID NO: 1 and the re-inserted psbA are different.

38. The method of claim 37, wherein expression of the product encoded by SEQ ID NO:1 is modulated by light.

39. An algal cell transformed by the method of claim 33.

40. The algal cell of claim 39, wherein the alga is *Chlamydomonas reinhardtii*.

41. An algal extract obtained from an algal cell transformed by replacing an endogenous chloroplast gene via integration of a chimeric construct having a heterologous coding sequence, a promoter sequence cognate or non-cognate to the endogenous chloroplast gene, and at least one UTR, wherein the endogenous chloroplast gene is re-inserted at a silent distal site.

42. The algal extract of claim 41, wherein the replaced gene is psbA and a product encoded by the heterologous coding sequence is a peptide as set forth in SEQ ID NO:2.

43. The algal extract of claim 42, wherein the peptide comprises approximately 0.25% to about 6% of the total protein in the extract.

44. The algal extract of claim 41, wherein the alga is *Chlamydomonas reinhardtii*.

45. A method of expressing a gene comprising:
transforming an algal cell by replacing an endogenous chloroplast gene via integration of a chimeric construct having a heterologous coding sequence encoding mammary associated serum amyloid A3 (M-SAA3), a promoter sequence cognate or non-cognate to the endogenous chloroplast gene, and at least one UTR, wherein the endogenous chloroplast gene is re-inserted at a silent distal site; and
cultivating the transformed algal cell under conditions to allow for expression of the chimeric construct.

46. The method of claim 1, wherein the heterologous coding sequence is driven by a non-cognate promoter of the endogenous chloroplast gene.

47. The method of claim 46, wherein the endogenous chloroplast gene re-inserted at the distal site is driven by a non-cognate promoter.

48. The method of claim 46, wherein the endogenous chloroplast gene re-inserted at the distal site is driven by a cognate promoter.

49. The method of claim 47, wherein a gene product of the heterologous coding sequence is repressed.

50. The method of claim 48, wherein expression of a gene product encoded by the heterologous coding sequence is not repressed.

51. A method of expressing a gene comprising:
transforming an algal cell by replacing an endogenous chloroplast gene via integration of a chimeric construct having a heterologous coding sequence, a promoter sequence cognate or non-cognate to the endogenous chloroplast gene, and at least one UTR, wherein the endogenous chloroplast gene is re-inserted at a silent distal site and driven by a non-cognate promoter; and
cultivating the transformed algal cell under conditions to allow for expression of the chimeric construct.

* * * * *